United States Patent
Alfano et al.

(10) Patent No.: US 10,495,629 B2
(45) Date of Patent: Dec. 3, 2019

(54) BEAD MILL AND METHOD OF USE

(71) Applicant: BLAZE MEDICAL DEVICES, INC., Ann Arbor, MI (US)

(72) Inventors: Kenneth Alfano, Canton, MI (US); Michael Tarasev, Pinckney, MI (US); Steven Meines, Grandville, MI (US); Terrance Boyd, Jackson, MI (US); Aaron Kehrer, Ypsilanti, MI (US); Gene Parunak, Saline, MI (US)

(73) Assignee: Blaze Medical Devices, Inc., Ann Arbor, MI (US)

( * ) Notice: Subject to any disclaimer, the term of this patent is extended or adjusted under 35 U.S.C. 154(b) by 227 days.

(21) Appl. No.: 14/773,137

(22) PCT Filed: Jan. 22, 2014

(86) PCT No.: PCT/US2014/012583
§ 371 (c)(1),
(2) Date: Sep. 4, 2015

(87) PCT Pub. No.: WO2014/137499
PCT Pub. Date: Sep. 12, 2014

(65) Prior Publication Data
US 2016/0011171 A1   Jan. 14, 2016

Related U.S. Application Data

(60) Provisional application No. 61/773,790, filed on Mar. 6, 2013.

(51) Int. Cl.
*G01N 33/49* (2006.01)
*B01L 3/00* (2006.01)
(Continued)

(52) U.S. Cl.
CPC .............. *G01N 33/49* (2013.01); *B01L 3/508* (2013.01); *B02C 19/06* (2013.01); *G01N 3/08* (2013.01);
(Continued)

(58) Field of Classification Search
CPC ........... G01N 33/49; G01N 21/17; G01N 3/08
See application file for complete search history.

(56) References Cited

U.S. PATENT DOCUMENTS 4,063,903 A * 12/1977 Beningson ............ B02C 17/007
44/629
5,147,612 A * 9/1992 Raal ........................ B01F 3/022
137/88
(Continued)

FOREIGN PATENT DOCUMENTS

| WO | 01/58432 A1 | 8/2001 |
|---|---|---|
| WO | 2005/077511 A2 | 8/2005 |
| WO | 2008/104916 A2 | 9/2008 |

OTHER PUBLICATIONS

Thermofisher, http://tools.thermofisher.com/content/sfs/manuals/User-Guide-2752-NanoDrop-Lite-UG.pdf. (Year: 2012).*
(Continued)

*Primary Examiner* — Matthew D Krcha
(74) *Attorney, Agent, or Firm* — Reising Ethington P.C.

(57) ABSTRACT

A bead mill and an associated bead-mill-based machine for testing mechanical fragility of red blood cells, employing a cartridge configured to contain a sample while cells get stressed via bead oscillation and, in the case of the fragility testing machine, also while lysis levels get detected, for presentation of fragility information.

14 Claims, 29 Drawing Sheets

(51) Int. Cl.
  *B02C 19/06* (2006.01)
  *G01N 3/08* (2006.01)
  *G01N 21/17* (2006.01)

(52) U.S. Cl.
  CPC ..... *G01N 21/17* (2013.01); *G01N 2203/0087* (2013.01); *G01N 2203/0089* (2013.01)

(56) References Cited

U.S. PATENT DOCUMENTS

| | | | |
|---|---|---|---|
| 5,630,557 A * | 5/1997 | Barthelmess | B02C 17/161 241/171 |
| 6,659,637 B2 | 12/2003 | Friedman | |
| 7,790,464 B2 | 9/2010 | Tarasev | |
| 8,142,067 B2 | 3/2012 | Dorado Gonzalez et al. | |
| 8,268,244 B2 | 9/2012 | Tarasev et al. | |
| 2003/0025018 A1 * | 2/2003 | Mashburn | B02C 17/10 241/175 |
| 2004/0053319 A1 * | 3/2004 | McWilliams | C12N 15/1003 435/6.18 |
| 2004/0241736 A1 * | 12/2004 | Hendee | A61B 5/14557 435/6.11 |
| 2006/0121603 A1 | 6/2006 | Yuan et al. | |
| 2010/0151512 A1 | 6/2010 | Huemer | |
| 2010/0184120 A1 * | 7/2010 | Tarasev | G01N 33/721 435/29 |
| 2010/0282059 A1 | 11/2010 | Van Dyke-Restifo et al. | |
| 2011/0300574 A1 | 12/2011 | Tarasev et al. | |
| 2012/0178121 A1 | 7/2012 | Tarasev et al. | |

OTHER PUBLICATIONS

Baskurt, Oguz K., Red Blood Cell Mechanical Stability, (Scientific Research Journal) Engineering, 2012, 5, pp. 8-10, (Published Online Oct. 2012 (http://www.SciRP.org/journal/eng).

Gu, Lei et al., Mechanical Fragility Calibration of Red Blood Cells, American Society of Artificial Internal Organs Journal, ASAIO J. May/Jun. 2005—vol. 51—Issue 3—pp. 194-201.

Kameneva, Marina V., et al., Mechanical Trauma to Blood, in: O.K.Baskurt, M.R.Hardeman, M.W.Rampling and H. J.Meiselman (Eds.), Handbook of Hemorheology and Hemodynamics, Amsterdam, Berlin, Oxford, Tokyo, Washington DC, 2007, pp. 206-227.

Harm, Sarah K. et al, Changes in Mechanical Fragility and Free Hemoglobin Levels after Processing Salvaged Cardiopulmonary Bypass Circuit Blood with a Modified Ultrafiltration Device, Journal of Extra-Corporeal Technology; 44, 1; pp. 21-25; Perfusion downunder by American Society of ExtraCorporeal Technology; 2012.

* cited by examiner

FIG. 7

| Device ID | | ← 1201 |
|---|---|---|
| Spectrophotometer calibration | | ← 1202 |
| LED calibration | | ← 1203 |
| LED hours | | ← 1204 |
| # Runs | | ← 1205 |

FIG. 12

| | | | |
|---|---|---|---|
| 1301 → | # repeats per rich parameter data point | PSR's per lysis cycle | ← 1302 |
| 1303 → | # spectra per repeat | # times the cmos sensor is 'scanned' per PSR | ← 1304 |
| 1305 → | Integration time per spectra | How long the cmos sensor is 'on' during each scan | ← 1306 |
| 1307 → | White LED power | Determined correct value for the White LED - Set Point | ← 1308 |
| 1309 → | 400nm LED power | Determined correct value for the 400nm LED - Set Point | ← 1310 |
| 1311 → | Acceptable starting hemoglobin range | # of RBC's per ml of fluid | ← 1312 |

FIG. 13

BEAD MILL AND METHOD OF USE

CROSS REFERENCE TO RELATED APPLICATIONS

This application claims the priority benefit of U.S. provisional patent application 61/773,790, filed Mar. 6, 2013, which is incorporated herein by reference in its entirety.

TECHNICAL FIELD

This disclosure relates to laboratory instruments and medical devices, and associated methods and components. More particularly, it relates to bead mills in general as well as associated tests for mechanical fragility of red blood cells.

BACKGROUND ART

The statements in this section merely provide background information related to the present disclosure. Accordingly, such statements are not intended to constitute an admission of prior art.

Red blood cell (RBC, erythrocyte) membrane fragility can be measured in various ways, principally either osmotically or mechanically. In general, it involves subjecting a sample of cells to a stress and measuring how much hemolysis occurs as a result of the applied stress. In the case of mechanical fragility (MF), cell membranes are exposed to some kind of mechanical disturbance such as a shear stress—which may vary in intensity, duration, or other parameters—while the proportion of cells lysing is tracked. This enables cells' overall susceptibility to hemolysis to be characterized and presented (comprehensively or selectively) in various ways. Fragility indices or profiles (single-parameter or multi-parameter) for erythrocytes may be desirable for research purposes or for clinical purposes. Applications may include blood product quality testing, diagnostics, clinical research, or basic research on RBC of humans or other species.

SUMMARY OF INVENTION

This section briefly and non-exhaustively summarizes certain subject matter of this disclosure.

This disclosure includes description of an MF tester configurable for testing erythrocyte membrane mechanical fragility, the machine comprising: a sample miller for moving a bead residing within a sample comprising erythrocytes within a stressing chamber, wherein the stressing chamber is configured to cause hemolysis in said sample; a chamber pincher for reversibly compressing an optically transparent portion of said stressing chamber to a thickness(es) suitable for an optical measurement to quantify said hemolysis; an optical detector for said optical measurement to quantify said hemolysis; and a light source for said optical detector.

The sample miller can include various configurations of cams (e.g. scotch yoke), or non-cam mechanical linear actuators, or non-mechanical linear actuators can present some alternative sorts of bead-milling mechanisms. In this respect, this disclosure pertains to an integratable, general-purpose mechanical fragility testing system utilizing a bead mill principle or the like for stressing the samples. In some embodiments, a motion-control system provides directly or indirectly lysis-inducing movement, while also providing upon defined intervals of stress sufficient optical proximity for effective detection of the extent of resultant lysis in a given sample of cells being tested. Moreover, in some embodiments no fluidic transfer is needed between stressing and detection of respective portions of a sample, and/or a disposable cartridge is employed to house the sample during testing. Another class of aspects or embodiments may involve a magnetic or electromagnetic bead mill, some embodiments of which allow moving a bead within a sample without needing to move the cartridge or any associated carriage.

Chamber pincher embodiments include, for example, vertical poles on one or two lateral sides of the cartridge, with a pole on both sides being preferred for stronger and more uniform and stable compression. In this case, a top and/or a bottom bar having flat surfaces may slide vertically toward each other by sliding at least one of them (with a rigid probe accompanying or embodying the fiber optic from at least one vertical direction, e.g. to enable pushing down on the flexible tube/chamber), driven by a stepper motor, to compress the chamber for optical detection when needed. Alternatively, the orientation of components can be altered such that the pinching occurs horizontally, or any other known pinching mechanism could be substituted and adapted appropriately.

Optical detector embodiments include, for example, a Spectrophotometer configured to measure light absorption, such as for example in a wavelength range of about 390-460 nm if using the preferred spectral approach described herein. Alternatively, a spectrometer may be configured to measure scatter, or the optical detector may be a cell counter utilizing light microscopy. Light source embodiments include, for example, a 420 nm and a white (e.g. 4000-5500 Kelvin) Light Emitting Diodes (LEDs), or other appropriate LED configurations, or bright-field microscopy bulbs (all depending in significant part, of course, upon the optical detection means and approach being employed). The pincher ensures that fiber optics from the top (e.g. illuminating fiber) and bottom (e.g. detecting fiber) of the chamber get near enough to each other to enable the optical detection/measurement.

This disclosure also includes description of a sample-holding cartridge for an MF tester, the cartridge comprising: a cartridge body for containing a sample, said cartridge body comprising an optically transparent material at a place where at least a portion of said sample can be reversibly dispersed upon pinching to be a thickness(es) suitable for optical detection of red blood cell hemolysis, said optically transparent material being flexible, or compressible, or being in direct or indirect connection with a flexible or compressible portion; and a bead(s) for milling said sample within the cartridge.

In some embodiments, said cartridge is "multiplexed" and thus comprises multiple such cartridges in combination together for testing distinct samples and/or for testing sub-samples of a given sample(s), perhaps simultaneously to conserve time and/or effort. In this respect, this disclosure pertains to a sample-holding cartridge, preferably disposable, and preferably single-use to minimize cleaning or risk of contamination (as for non-multiplex cartridges as well), for the aforementioned testing system, which may comprise an optically transparent portion at an area of said cartridge where said sample can be brought to dispersed or thinned to achieve a thickness which may or may not be predetermined (depending on the approach for this used in a given embodiment) upon a pinching of said cartridge, said optically transparent portion being either also a flexible portion and/or in direct or indirect contact with a flexible portion to facilitate said pinching—which may be temporary or reversible so as to enable repeated such pinching, either between different extents of mechanical stress application and/or for repeat measurement any given single point of the same.

This disclosure also includes a description of an electromagnetic (EM) bead mill, of the kind employed in some embodiments herein of an MF tester, and which is also utilizable alone for any general purpose for which bead mills are currently used (e.g. disruption of a biological sample). The present EM bead mill comprises a holding place for positioning a cartridge containing a sample and a bead, and an electromagnet configured to cause said bead to oscillate within said cartridge, to disrupt said sample. Preferred embodiments of the EM based embodiments utilize adaptations of existing developed audio transducers to produce the EM fields. The configuration can be set to work by either moving the entire cartridge, in which case the bead would not need to be magnetic, or it can be set to just move the bead, in which case the cartridge could remain still and the bead would need to be sufficiently magnetic. Unlike the use of beads in ultrasound-based cell disruption, which (when supplemented with beads) typically utilizes beads no more than about 500 microns in diameter induced to oscillate by ultrasound in the kHz-MHz (i.e., at least 1000 Hz) frequency range, the bead(s) in the present bead mill should be larger and/or heavier, at least one or more millimeter(s) in diameter, with oscillating frequencies in the Hz (under 1000 Hz) range. Moreover, the present invention is capable of providing non-ultrasonic bead-induced mechanical shear stress to the sample. In the case of a general bead mill, the vial or tube or cartridge is typically a single-use disposable product (simpler than the cartridges needed for fragility testing), and in those cases the bead is typically reusable. Associated methods include using the system to measure RBC MF, and also making the sample-holding cartridge.

The scope of the invention is defined by the claims, which are incorporated into this section by reference. A more complete understanding of the present disclosure (including other filings that are incorporated herein by reference) and associated embodiments will be afforded to those skilled in the art, as well as the realization of additional advantages thereof, in consideration of the overall disclosure including drawings where applicable. Reference will be made to the appended sheets of drawings that will first be described briefly.

BRIEF DESCRIPTION OF THE DRAWINGS

All drawings are for illustrative and explanatory purposes only and not intended to limit the present invention to any of the example embodiments depicted.

FIG. 7 shows the pre-run screen with planned data point collection times.

FIG. 12 shows an example of a data structure.

FIG. 13 shows a settings embodiment.

MODE(S) FOR CARRYING OUT THE INVENTION

Figure 1:
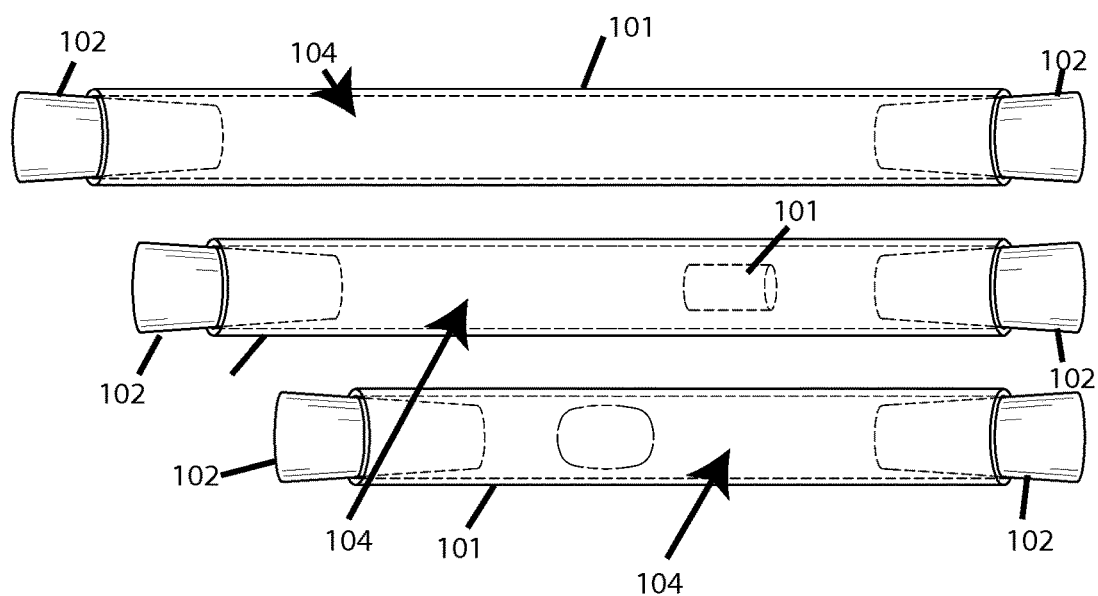
FIG. 1 shows embodiments of a sample cartridge.

This section contains descriptive content for this disclosure. It is also to be understood that the terminology and phraseology used herein is for explanatory and exemplary purposes and not intended to be limiting.

Erythrocyte mechanical fragility testing combines controlled physical (and more specifically, mechanical) stressing of cells along with a measurement of how much hemolysis occurs during such stressing. A wide range of research and clinical applications are possible for such metrics. There are many ways to provide the mechanical stress in a fragility assay, as well as many ways to measure the resulting hemolysis. Mechanical fragility testable by utilizing a low-energy mechanical stress such as via bead mill, tends to more directly reflect erythrocyte membrane properties (as compared to high-energy mechanical stress such as via ultrasound). Sometimes stressors can be combined, such as when evaluating changes in mechanical fragility under differing osmolarities; relatedly, temperature or pressure or other factors can in some cases be relevant stress conditions.

There are also many ways that a fragility assay can in effect measure the hemolysis resulting from the mechanical stress. One way is by cell counting before and after a given stressing interval (discussed for example in US Patent Application Publication No. US20110300574, incorporated herein by reference in its entirety). Such an approach could use any known principle of cell counting, preferably optical, such as those using light microscopy like the commercial Cellometer™ line. But whenever the particular advantages of cell-counting are not needed or desired, the preferred approach herein is to use the Blood Hemolysis Analyzer invented by Michael Tarasev and discussed for example in U.S. Pat. No. 7,790,464, issued Sep. 7, 2010, incorporated herein by reference in its entirety. This approach exploits the fact that the spectral peak in the Soret region (un)flattens in relative proportion to the extent of hemolysis in a given sample. [This optical system/method involves projecting light into a sample to allow the light to pass through the sample, wherein a first portion of the light, having a wavelength of about 390-460 nm, is absorbed by a cell-free hemoglobin derivative, and a second portion of the light, having a wavelength of about 390-460 nm, is absorbed by a cellular hemoglobin derivative contained within erythrocytes; and measuring light absorption with an absorption detector configured to determine the light absorption of the sample, within a wavelength range of about 390-460 nm, and to provide an at least partially flattened spectra commensurate with the ratio between cell-free and cellular hemoglobin, to thereby determine the relative cell free hemoglobin concentration within the sample, from which the proportion of hemolysed cells can then be inferred.] This notably avoids the need for any separation steps such as for example centrifugation or other known means for separating solid from liquid elements; the main aspects of this approach involve utilizing a difference in apparent (not actual) spectral absorption between intracellular and extracellular hemoglobin, in order to infer what fraction of RBC in a given sample are lysed at a given time (of course, this unique approach to lysis measurement is only suitable for RBC). Another consideration is that determining fractional hemolysis requires knowing or measuring the original hematocrit or a reasonable proxy such as total hemoglobin concentration (which can be address by various possible means).

A fragility assay can involve outputting various kinds or amounts of fragility data—including specific values or indices, single-variable-parameter fragility profiles, and/or multi-variable-parameter ("multi-dimensional") fragility profiles. (Note that "parameter" can be used to refer to either a stress parameter or a fragility parameter.) Data matrices reflecting how much lysis occurs under various combinations of stress parameters can be used to give profile-based parameters characterizing the sample tested (or the source it represents). Data of interest could comprise how much lysis would be expected under a given set of stress parameters, what stress condition(s) would be expected to result in a given lysis level, or slopes or shapes of any such curves/trajectories—the latter of which can reveal subpopulations within a sample with their own discernible profiles. The particular fragility parameter(s) sought will likely depend on what is deemed most clinically or scientifically relevant for each particular application. Notably, a single-value index parameter can itself be determined from a profile, such as through an interpolation.

Depending on the stress/lysis method employed for a given MF testing approach, it may be important to dilute samples to ensure that all samples (or subsamples) have the same concentration of red cells (hematocrit) in order to have consistency in the rate/efficiency of hemolysis when subjected to stress. Additionally, such dilution can be used to ensure the uniformity of the cells' environment when comparing different RBC samples. Another consideration is that dilution may be be necessary to bring the spectral absorbance of the RBC or blood sample within the dynamic range of the detection system used (e.g. cell counting apparatus or spectrophotometer). Also, in the case of red cell samples experiencing aggregation or coagulation, it can be useful to ascertain the role of such on the cells' susceptibility to induced hemolysis, along with the overall biochemical and fluidic environment in any given sample of cells.

Sensitivity with regard to spectrally-based measures of hemolysis can be enhanced by accounting for multiple forms of hemoglobin (Hb)—namely oxy, deoxy, meth, and/or carboxy Hb forms. Oxygenated (Oxy) Hb typically constitutes the vast majority in aerated blood or RBC, with other Hb forms present in negligible amounts. It's uncommon to determine the concentration of all four types, and could be unnecessary for the amount of precision typically needed, but nevertheless remains an option that could be implemented with sufficient spectral resolution. Multi-wavelength analysis methods for such implementation are well known. The main three wavelengths used in the preferred optical approach include 418 nm (the peak of the soret region), 576 nm (the peak for oxy Hb), and 685 nm for a base-line. Other absorbent proteins (e.g. bilirubin) that may potentially interfere with hemoglobin measurements can also be accounted for with multi-wavelength analysis, if desired, and overall sensitivity can potentially be enhanced by using first and second derivatives of the optical spectra.

Benefits pertaining to various desirable aspects of RBC MF testing can be substantially enhanced by employing a disposable chip or cartridge component or the like to self-contain the blood sample during testing; usage in general of a disposable component in RBC mechanical fragility testing is a principal focus of U.S. patent application Ser. No. 13/708,980, Publication US20130098163, filed Dec. 8, 2012, which is hereby incorporated by reference in its entirety. However, this present disclosure specifically describes disposable cartridges that are configured to be used with bead-mill based systems. [U.S. Pat. No. 8,268,244, which is hereby incorporated by reference in its entirety, discloses a concentric-cylinder based approach to such cartridge based modularization (e.g. FIGS. 3 and 4 of that patent)—in that context targeting assessments of RBCs' quality or transfusion suitability.]

Two kinds of possible approaches for agitating a bead in a "bead-mill-based" approach to lysing cells can include a motor/CAM approach which shakes the sample containing the bead, or an electromagnetic-field based approach to actuating the bead's movement within the sample (directly or indirectly). These are both compatible with using a disposable (ideally single-use) sample cartridge that can serve in effect as both a stressing chamber (for applying mechanical stress) and an optical cuvette (for measuring lysis or indicia thereof). [Various experiments and certain other research discussed or referenced in the description herein were conducted by one or more co-inventor(s), sometimes with assistance from other technical personnel of applicant company or a contracted service provider(s), and may include experiments done via test-beds, preliminary subsystems, mock-ups, or anything else whose results may be potentially relevant to the present disclosure.]

This disclosure next describes an electromagnetic approach to stressing a test sample, specifically by actuating the bead, which some embodiments may utilize. There are situations where its advantages (e.g., less moving parts and vibration and noise, potentially smaller size and less ramp-up/ramp-down time for oscillation speed, etc.) prove worthwhile. Of course, any particular system's specifications are likely to be significantly configuration-specific; hence generalizable principles are explained here using empirical and/or other research results, from which appropriate adaptations may be inferred and extrapolated as needed. The experiments discussed here next aid with understanding how to adapt various EM configurations as needed for various possible bead-milling applications.

An electromagnetic (EM) bead mill can use a changing magnetic field as the method of moving a magnet in a fluid. In a preliminary setup and associated experiments, two 12 volt solenoids opposing each other were used. These were powered by a function generator which alternates the current direction according to a chosen frequency. A switching circuit controlled the fields of both solenoids, so at any given point in time one solenoid was pushing the magnet away from it, and the opposing solenoid was pulling the magnet towards it. The bead was suspended in a fluid contained by the plastic tube.

A test was performed in order to see the effects of different variables on the displacement of the magnet during one period of oscillation. The variables considered were the voltage applied across the solenoids, the distance between the solenoids, the frequency applied, and the offset of the tube from the central solenoid axis. The displacement of the bead magnet was calculated by taking high speed video of the bead oscillating in the tube with a steel rule in frame. In order to keep the tube centered for different solenoid-to-solenoid distances, 3 different length tubes were used. FIG. 1 depicts examples of such tubes 101, each with plugs 102 on the ends and a magnetic bead 103 inside with liquid 104. It also illustrates conceptually how an electromagnet can be positioned (externally) relative to such tubes, to force the contained magnet's movement on-demand.

As voltage applied increased, the displacement at a constant frequency generally increased. As solenoid distance increased, displacement at a constant frequency decreased. As frequency increased, displacement at a constant voltage decreased. An offset from the central solenoid axis decreases displacement. As the solenoid distance increased, the rate at which the displacement increased per volt applied at a constant frequency decreased.

The closer the solenoids were, the stronger the force on the bead was, and the higher the displacement for a constant voltage and frequency. Another observation was that the rate at which the displacement increased per volt at a given frequency was also higher. The slopes of the displacements were found by taking linear trend lines of the displacement vs. voltage graphs for each of the three distances tested.

The results from 60 Hz measurements at low voltages were at the threshold of the digital scale resolution. The testing approach would need to be modified for applications where reliable data from this frequency range is essential. However, for most expected applications, 30 Hz is likely to be sufficient (for the high end of intensities to be employed). The slope of the displacement vs. voltage curve could in principle be used to find the voltage needed for a specific displacement, but this would involve a working assumption of linearly proportional behavior of the bead in a fluid. For maximum displacement, if desired, the frequency should be low, the solenoid distance minimized (or a single-solenoid with alternating current can be used), the voltage maximized, and the tube centered on the solenoid axis. Repulsive as well as attractive magnetic force could potentially be utilized.

Also significantly, other experiments showed that, in contrast to when the entire cartridge/sample is moved to move the bead indirectly (whether via CAM or magnetism), moving the bead "directly" in this manner introduces more possibility for separation of the parameters for force or sustained bead "velocity" versus motion "amplitude" or net relative bead movement, both of which can be affected by oscillation "frequency," which should be taken into account if "intensity" of stress is desired to be truly a significantly separate parameter from aggregated net "duration" (the true total and distribution of which can also to some extent be a function of "frequency.")). Finally, issues with power needed (and thus heat generated also) can be alleviated by configuring the electromagnet(s) such that the field is optimal for efficient longitudinal bead oscillation. [See later below for additional description of particular EM-based approaches, including utilizing available off-the-shelf motion actuators.]

Another class of magnetically-based embodiments for a bead mill (or a bead-mill-based MF tester) involves having mechanical motion outside of the sample chamber that corresponds to moving a (non-electro) permanent magnet within the chamber (i.e., analogous to magnetic stir bars). This could comprise counter-rotating discs just outside either side of the cartridge, with permanent magnets placed to engage the bead at respective points in its journey. In a preliminary test-bed prototype evaluated for this approach, a magnet outside the cartridge on each side was able to controllably "carry" the magnet back and forth with good reliability and reasonable positioning tolerances at a target frequency of 30 Hz or oscillations/sec. Notably, magnetically trapping the bead between magnets for such carrying proved more controllable—especially at higher frequencies—than either "pushing" or "pulling" via direct attraction or repulsion.

This disclosure next describes certain example approaches and embodiments for a motorized cam-based approach to agitating the bead. Two example kinds of motorized approaches evaluated include a "horizontal" bead shaker/mill and a "vertical" one, using respective versions of the TissueLyser™ commercial bead mills sold by Qiagen.

The horizontal version has two cam driven arms that create a horizontal motion (somewhat non-linear, due to angular or partially-circular motion) to drive a bead in a sample tube, and it is used for some of the present experiments because some embodiments of the present system employ some of its principles. To compare the motion of the bead in this mechanically driven lyser with that of the aforementioned EM approach, high-speed video (HSV) of the moving bead was taken and analyzed. Initial tests were run using a 5 mm stainless steel bead in a solution of buffer with Albumin. It was found that at higher oscillation frequencies the solution foamed too much to be able to see the bead. Subsequent runs were performed using buffer without Albumin (in general, the biochemical environment of RBC during the testing can notably impact lysis efficiency, which should be taken into account in a testing protocol). Also notable is that the angular/semi-circular nature of the motion resulted in some inconsistent stress application at different locations in the holder of the multiple samples.

High speed video was employed to determine the ramp up and ramp down time lengths at the beginning and end of each discrete stressing interval, as this also needs to be accounted for when adapting any bead milling technology to a fragility test which requires accurate knowledge and quantitation of stress being applied. This presents another advantage for direct EM driven movement of the bead itself.

As with the horizontal mill, the vertical mill is not specifically designed for "fragility" testing purposes and hence experiments were needed to assess the relative suitability to be adapted for sufficiently precise and controlled application of mechanical stress on-demand. And conversely, of course, any kind of new or custom lyser for a fragility tester is likely to be readily adequate to perform basic and generalized bead-milling functions if desired (and in some cases may do so more desirably).

Figure 2:
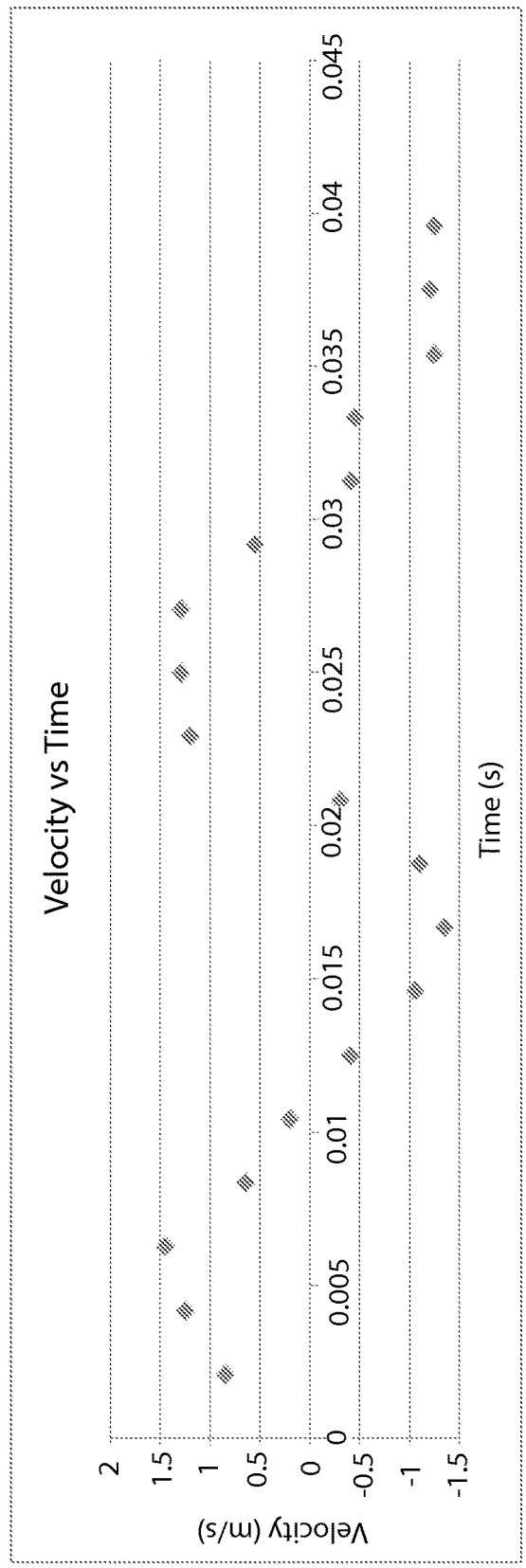
FIG. 2 shows a chart of bead velocity versus time.

The vertical mill was analyzed to find the frequency of oscillation and the velocity of the mill. Velocity vs. time was plotted for the vertical bead mill, with the plot 200 shown in FIG. 2. The vertical bead mill is comprised of an electric motor with a horizontal output shaft connected to a cam. The bead/tube carriage is threaded onto a vertical shaft connected to the cam. There is a control circuit board that handles the numerical display on the top of the frequency and timer, and also a feedback circuit to regulate the motor speed with information from an encoder on the motor. Other notable differences between vertical and horizontal bead mill approaches such as those above include that, in a vertical bead mill, the bead comes out above the surface of a liquid sample and impacts said surface upon every re-entry. This of course assumes that the tube is not entirely filled, yet with a horizontal approach the fluid dynamic implications are different in that even an un-filled tube would not result in such periodic separation of the bead from the sample.

Overall, for adapting these two example cam bead bills to mechanical fragility (MF) testing, the greater linearity of the vertical approach is preferable to the angular movement of the horizontal mill (due to the greater accuracy/consistency), yet all else being equal a horizontal motion is more conducive to the preferred approaches to optical detection.

This disclosure next conceptually describes an example embodiment for an overall MF testing system; such embodiments feature essentially linear (i.e., non-angular) and horizontal motion of a sample/cartridge/carriage, to shake a bead, to induce sample rupture. Associated example embodiments of particular (often changeable) sub-systems for this are briefly explained first in principle, before being described later in the context of drawings. This example embodiment (various aspects and optional features of which can be selectively employed and/or mixed-and-matched in enumerable combinations or permutations, to comprise various possible embodiments) can be thought of as involving the following six sub-systems.

First, an optics sub-system contains a spectrometer connected to the electronics or PC, and elements to generate and collect light from the sample and focus it on the spectrometer. Custom and/or off-the-shelf light sources and/or spectrophotometers may potentially be employed. Some combination of half-silvered mirrors, dichroic mirrors, and/or beam-splitters might be employed.

Second, a "sampling" or "pinching" sub-system contains two moving (or one moving and one stationary) elements that pinch the cuvette. These elements contain fiber optics to deliver and collect light from the sample, and mechanical stops to set a particular optics gap during pinch/release cycle (unless pinching essentially to contact with readings collected serially during each compression or de-compression, or compressing until reaching a predetermined reading based on spectral characteristics of such compressed sample irrespective of the actual gap magnitude), with two linear actuators that control the position of the moving elements. After pinching, they are used to retract the moving elements out of the way so lysing can occur. There is also an electromagnet that can pull the bead to one side of the cuvette during pinch/release cycle (in some embodiments this function may be achieved via gravitational tilt/pause, beveled "pusher," permanent magnet, or other means). Preliminary experiments also show that it is best to pinch in a manner (e.g. from the top down, maintaining a fixed/flat bottom) that prevents gravity from pulling the sample away from where readings will be taken, and decrease or minimize any intra-sample separation such as cell precipitation in an RBC suspension. The gap between compressed cartridge walls, and thus the thickness of the sample in the optically tested area, can be established based on the attenuation of the probing light, within the used spectral range, due to sample absorption and optionally scattering, such that the resultant changes in light intensity are within the dynamic range of the detection system (e.g. spectrophotometer). Alternatively, scattering, cumulative and/or within a set angular range can be used to evaluate the number of scatter-causing intact cells within the sample thus providing an estimate of hemolysis.

Third, a lysing (or stressing) sub-system contains a cuvette carriage that oscillates on linear rails. This carriage also has a slot for the cuvette to be inserted.

Fourth, a carriage motion sub-system contains a motor that controls the speed and position of the cuvette carriage during lysing, and also moves the cuvette to the correct position during pinch/release cycle.

Fifth, a cartridge or "cuvette" sub-system (which can also be deemed a distinct device) contains a container consisting of a membrane formed by two sheets of plastic film and a plastic overmold. The membrane is flexible to allow for stretching during sampling/pinching. This container can hold the blood and the bead during both lysis/stressing and optical detection (to find resultant lysis), thereby serving as both a stressing chamber and an optical cuvette. The container can be open at one end for loading of a sample; it also can comprise a cap that can screw on to the container after loading.

Sixth, an electronics sub-system contains motion-control circuitry for motor speed and angular position, and pinch/release circuitry for pinching linear actuators and switching the electromagnet on/off.

Figure 3:
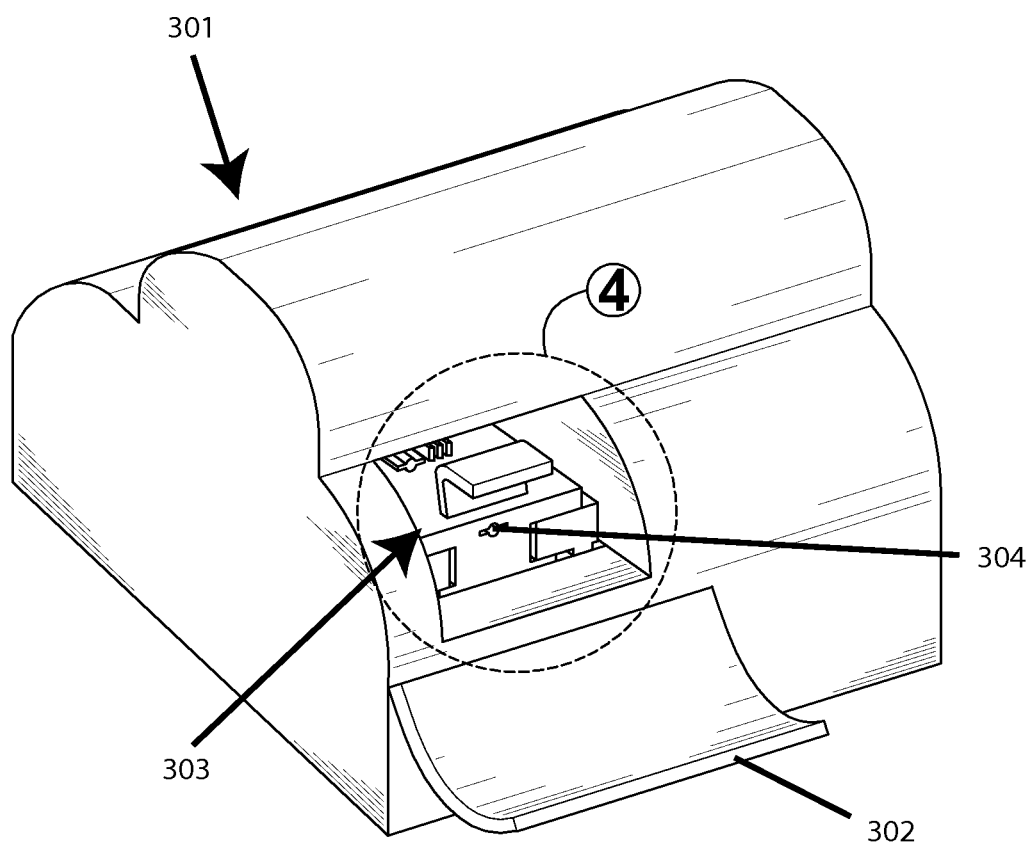
FIG. 3 shows a bead-mill-based MF tester embodiment, exterior view.
Figure 4:
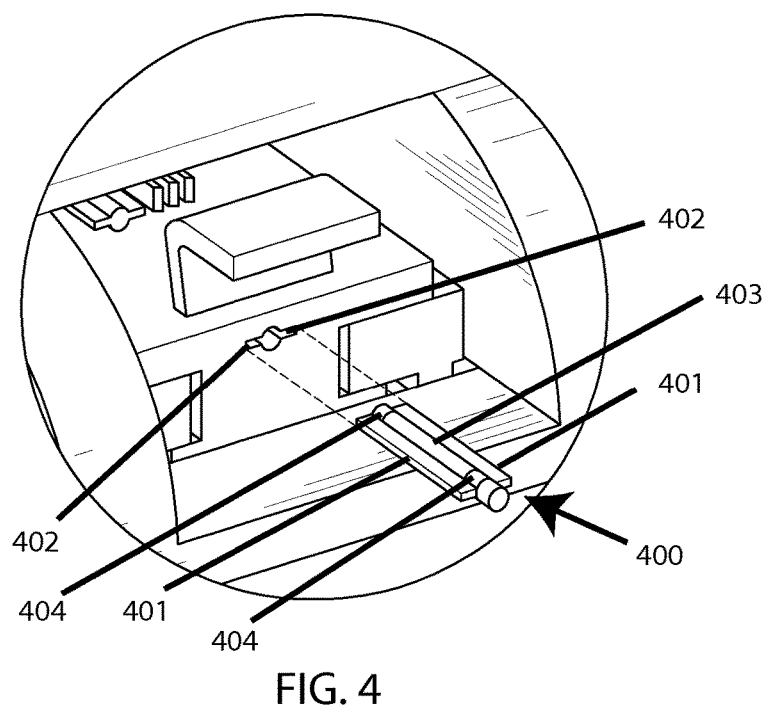
FIG. 4 shows a bead-mill-based MF tester embodiment, interior view.
Figure 5:
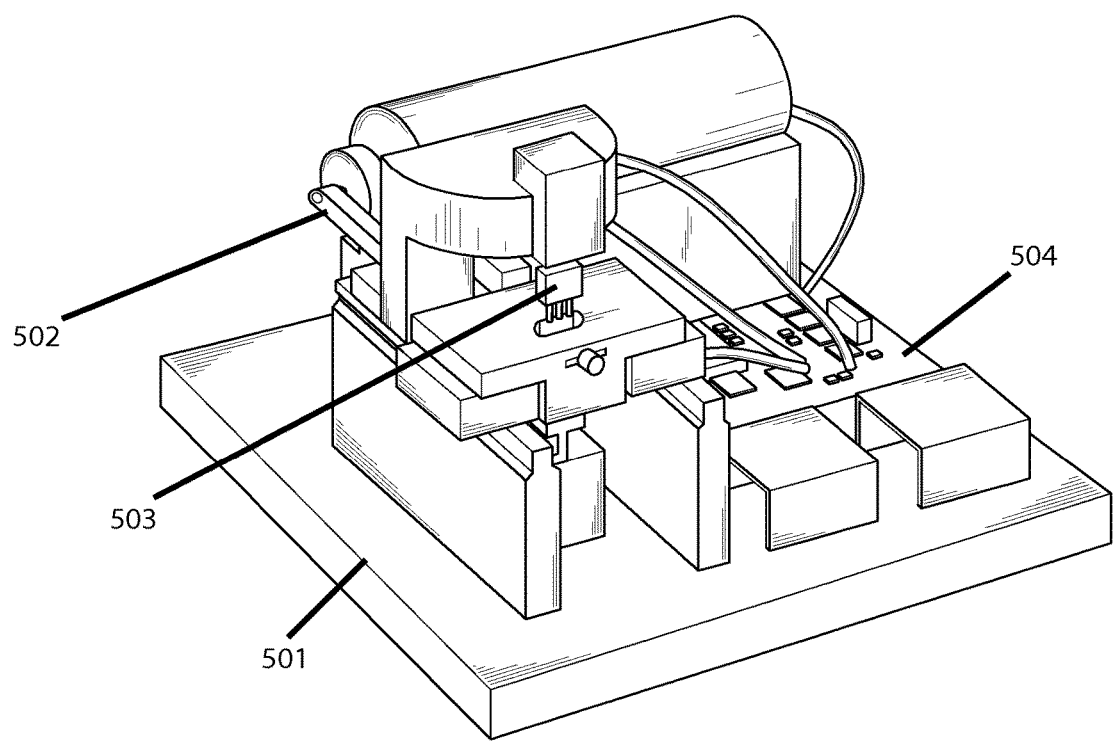
FIG. 5 shows a bead-mill-based MF tester embodiment, interior view without casing.

FIGS. 3-5 show a conceptual example system design. FIG. 3 shows an outer casing 301, on the front of which is a door 302 which here is open, thus exposing an access cavity 303, in which there is a port 304 for inserting a cartridge (not shown). Then FIG. 4 shows a zoom view of said access cavity, and shows a cartridge 400 for containing a testing sample, which features winged sides 401 to facilitate entry into corresponding slits 402 on said port, as well as a flexible and optically-transparent membrane portion 403 (in the middle) with a hard-plastic partial over-mold 404 for structural definition. FIG. 5 shows the interior of the system without said casing, thus exposing the base plate 501, a motor-driven cam 502 for horizontal agitation of said cartridge, a motor-driven pinching mechanism 503 for compressing said membrane portion for optical readings between agitation increments, and the control electronics 504.

The following listed conceptual steps are involved in this example machine's operation, each employing appropriate respective aspect(s) of the above-noted subsystems: pinch/release cycle, moving bead aside during pinch/release cycle, optics gap distance setting, cartridge insertion path, orienting cartridge to optics, accommodations for blood volume displaced during pinch/release, and disposable cuvette loading.

This disclosure next describes associated software for running RBC MF testing system embodiments such as introduced above, beginning with conceptual visualizations of software graphical interface screens (the examples shown here being for a research-use focused version of the system). [For the simulated screenshots, note that anything labeled "sonication" should herein instead read as "bead milling."] In many respects, these software related aspects are readily adaptable to various kinds of embodiments—or in some cases even non-bead-based MF testing. Note that on a high enough level of abstraction, the software that operates the overall system can generally be conceptually approached somewhat independently of the particular hardware and mechanics employed for the fragility testing unit—but at certain levels of detail they do become interdependent, and examples provided herein are intended to be illustrative and exemplary in a manner understood as adaptable in various ways consistent with the full range of possible embodiments.

Figure 6:
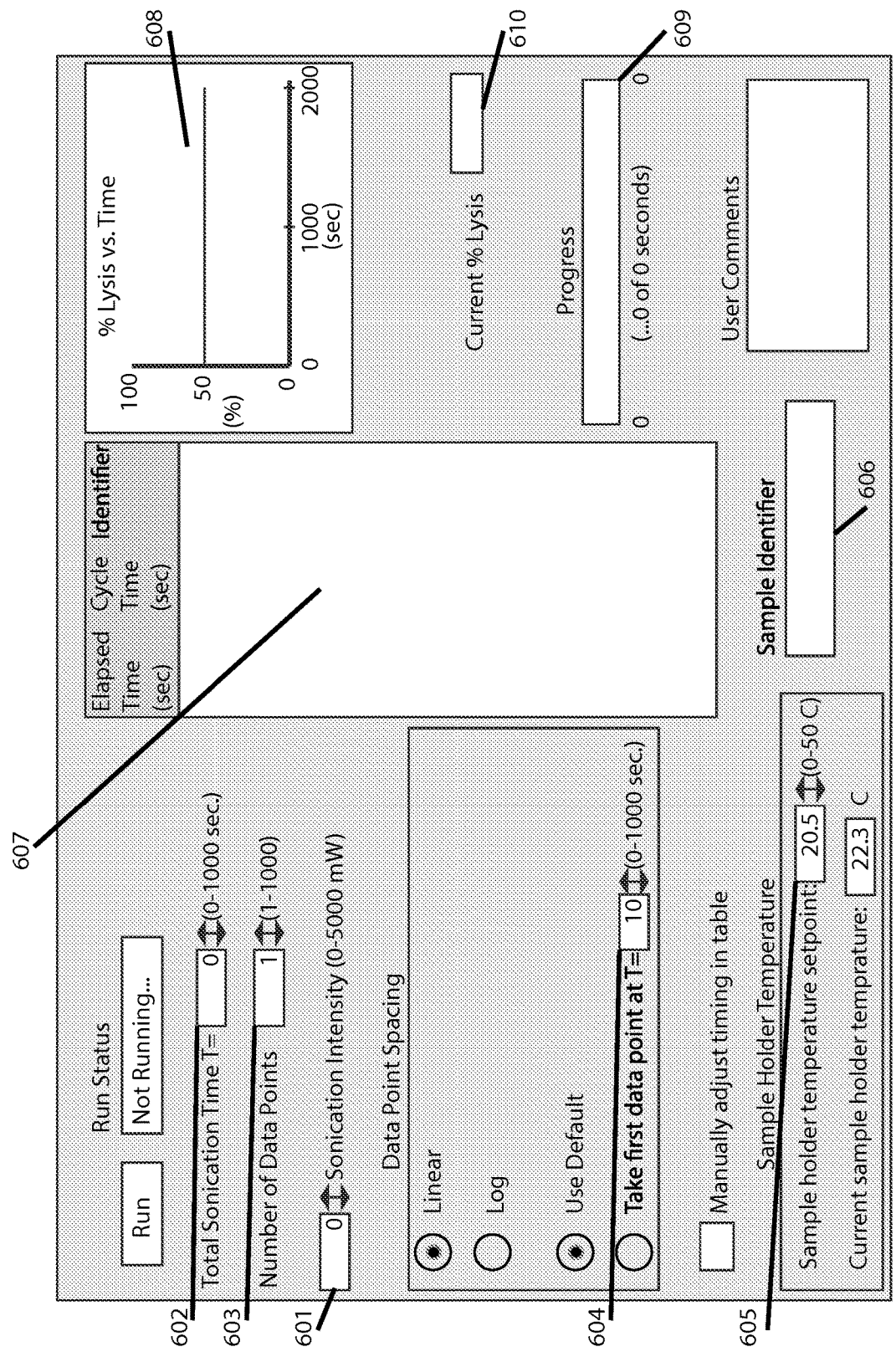
FIG. 6 shows a "pre-run" screen.

FIG. 6 shows a "pre-run screen." It contains a field box for the user to supply a run's key parameters including what level of stress intensity (should read here "Bead Oscillation Frequency, Hz") the device will provide 601, the total duration over which such stress will be provided 602, and the number of data-point intervals at which the stressing will pause to determine hemolysis level in the sample 603. Note that the timing/spacing of the data points, which will constitute the profile, can be customized with further user options 604. If desired, temperature of the test sample can be set and monitored via another sub-window 605. [Note that a temperature control system may be included in the device, at varying levels of sophistication employing established techniques, as desired, to provide users with a range of testing-temperatures to choose from (e.g. ~5-45 deg. C.). At a basic level, it may simply keep ambient room temperature maintained within an appropriate tolerance, such as via cooling fan(s) and perhaps thermal baffle(s).] Data points to be collected are listed along with identifiers (not to be confused with the sample's identifier box 606) in a display sub-window 607 and as collected will be plotted as a profile on a graph 608, while this progress is tracked with a progress bar 609 for operator information and convenience (relatedly, the cumulative amount of hemolysis in the sample is also reported nearby 610). (Note that the profile plot may be withheld, flagged, or disclaimed if unperformed mathematical correction or additional measurement would be needed for a particular sample in order to have acceptable accuracy.)

Figure 7:
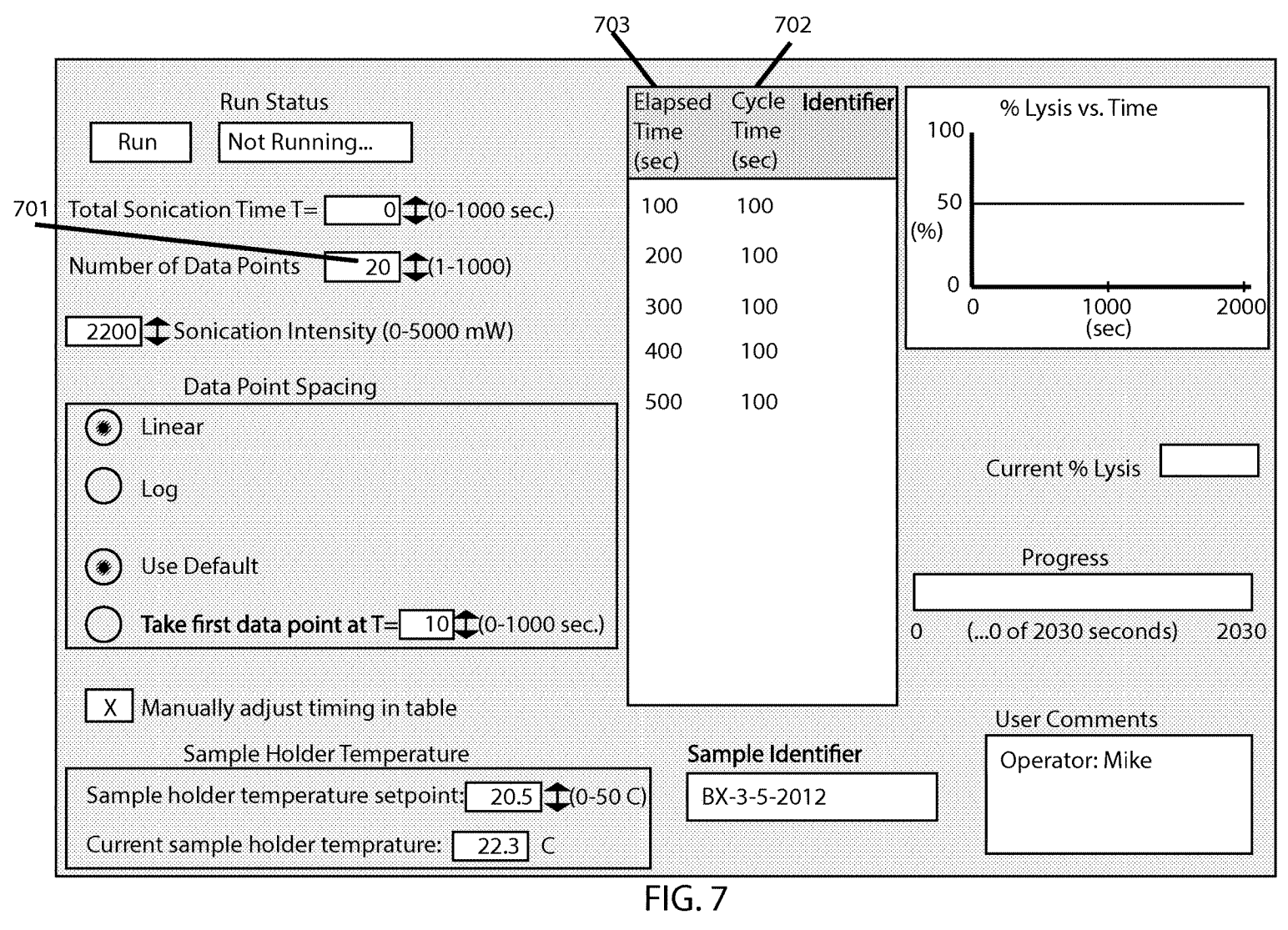

FIG. 7 shows the pre-run screen with planned data point collection times represented by numeric text 701 being manually adjustable (as opposed to using strictly linear or logarithmic data point spacing) upon being generated in said display sub-window. In this case, cycle time 702 refers to how much additional stressing occurs for each incremental data point, while elapsed time 703 refers to the cumulative amount of stress exposure for the sample up to any given point. And note that each data point may represent multiple measurements repeated (e.g. for averaging) at any given level of hemolysis.

Figure 8:
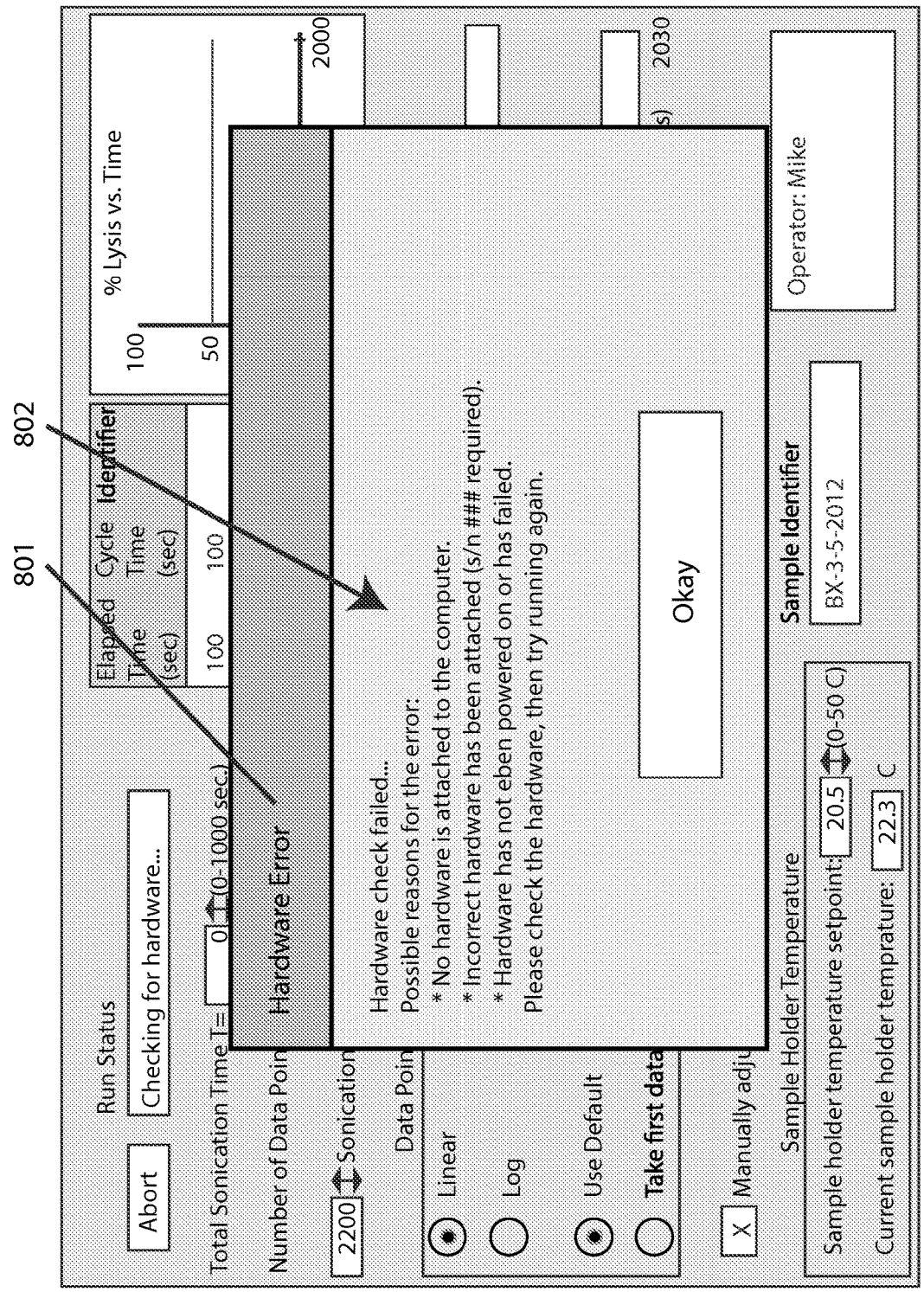
FIG. 8 shows an example screen with an attempted run that failed a hardware check.

FIG. 8 shows an example screen with an attempted run that failed a hardware check. The warning window 801 lists possible reasons 802 for the failure. This is an important aspect of integrating software that operates a special machine—as the software of the present invention is not merely abstract or computational. Relatedly, subsequent screen examples discussed below depict other system-related considerations such as the test sample's temperature monitoring and optical density; moreover, an error window (not shown) pops up if the loading door is not securely closed when attempting to run the system for a test.

Figure 9:
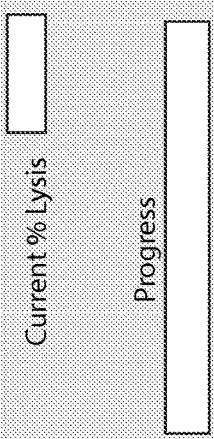
FIG. 9 shows the screen when the system is waiting for the temperature to reach the set point.

FIG. 9 shows the screen when the system is waiting for the temperature to reach the set point, as indicated by the run status bar 901 and system status button 902.

Figure 10:
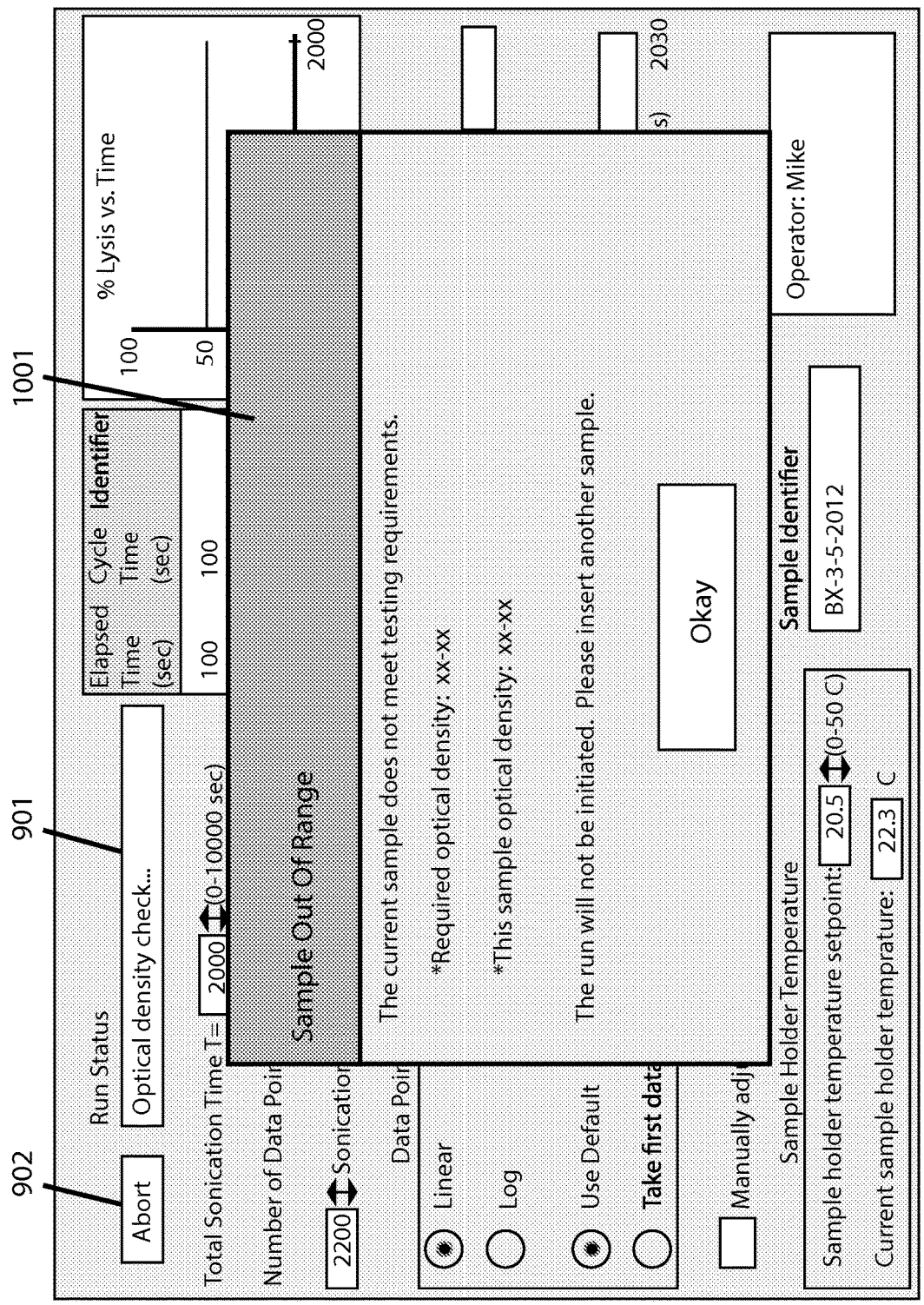
FIG. 10 shows the screen with a run attempt that has failed an optical density check.

FIG. 10 shows the screen with a run attempt that has failed an optical density check, as indicated by an appropriate warning window 1001 as well as said status bar 901 and status button 902.

Figure 11:
FIG. 11 shows the example screen with a run in-progress.

FIG. 11 shows the example screen with a run in-progress, as accruing data point identifiers are being added 1101 to said display window, with such data points being used for a partial profile 1102 in said graph, and a correspondingly filled portion 1103 of said progress bar.

Examples of data structures include FIG. 12 which covers example device-specific calibration and records, with field identifiers for Device ID 1201, Spectrophotometer calibration 1202, LED calibration 1203, LED hours 1204, and # Runs 1205.

FIG. 13 covers example settings, with field identifiers for # repeats per rich-parameter data point (a "rich parameter" being a stress parameter for which data points are more densely concentrated—which is often more easily so for stress duration versus stress intensity, for example) 1301, with the corresponding field value representing how many pinch-release cycles (repeats of squeezing the sample down to a readable gap-height) occur per such data point (lysis cycle) 1302; the # spectra taken per such repeat 1303, with the corresponding field value representing how many times a cmos sensor is scanned per pinch-release cycle 1304; the integration time per such spectra 1305, with the corresponding field value representing how long the sensor is on during each scan 1306; the white LED power 1307, with the corresponding field value representing the set point determined for such value 1308; the 400 nm power 1309, with the corresponding field value representing the set point determined for such value 1310; and the acceptable starting hemoglobin range 1311, with the corresponding field value representing the concentration of RBC in the sample fluid 1312.

Figure 14:
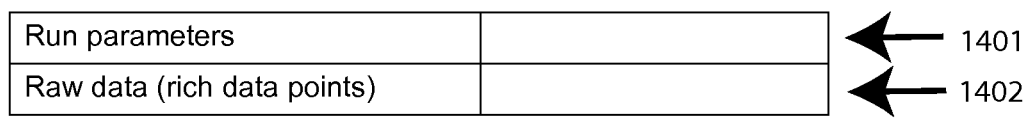
FIG. 14 shows a csv file with field identifiers.

As represented by FIG. 14, a ".csv" file may be employed with field identifiers for run parameters 1401 as well as for select raw data 1402.

This disclosure next addresses certain aspects of the software architecture for a MF testing system embodiment such as above—to help visualize the logical flow of operation in the software that controls the blood fragility unit (testing components), as well as the associated hardware and connections necessary to interface with the blood fragility unit. Graphical representations of the logical flow of the software during operation of the MF tester are accompanied by those also helping to visualize the main system hardware components of the blood fragility testing unit and the control computer and their connections to each other (system diagrams).

Figure 15:
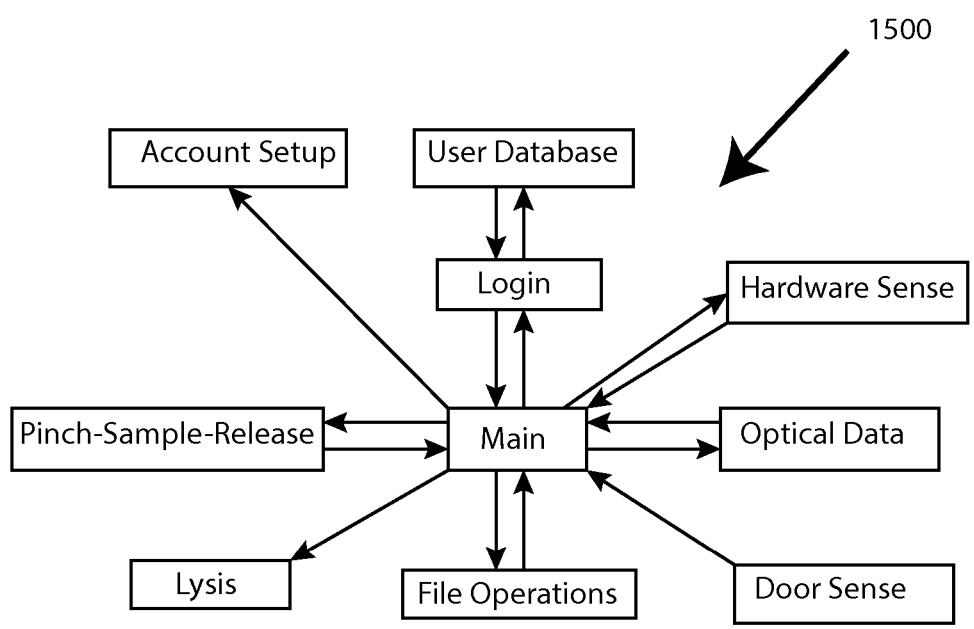
FIG. 15 shows a generalized software architecture diagram.

FIG. 15 shows a generalized software architecture diagram 1500.

Figure 16:
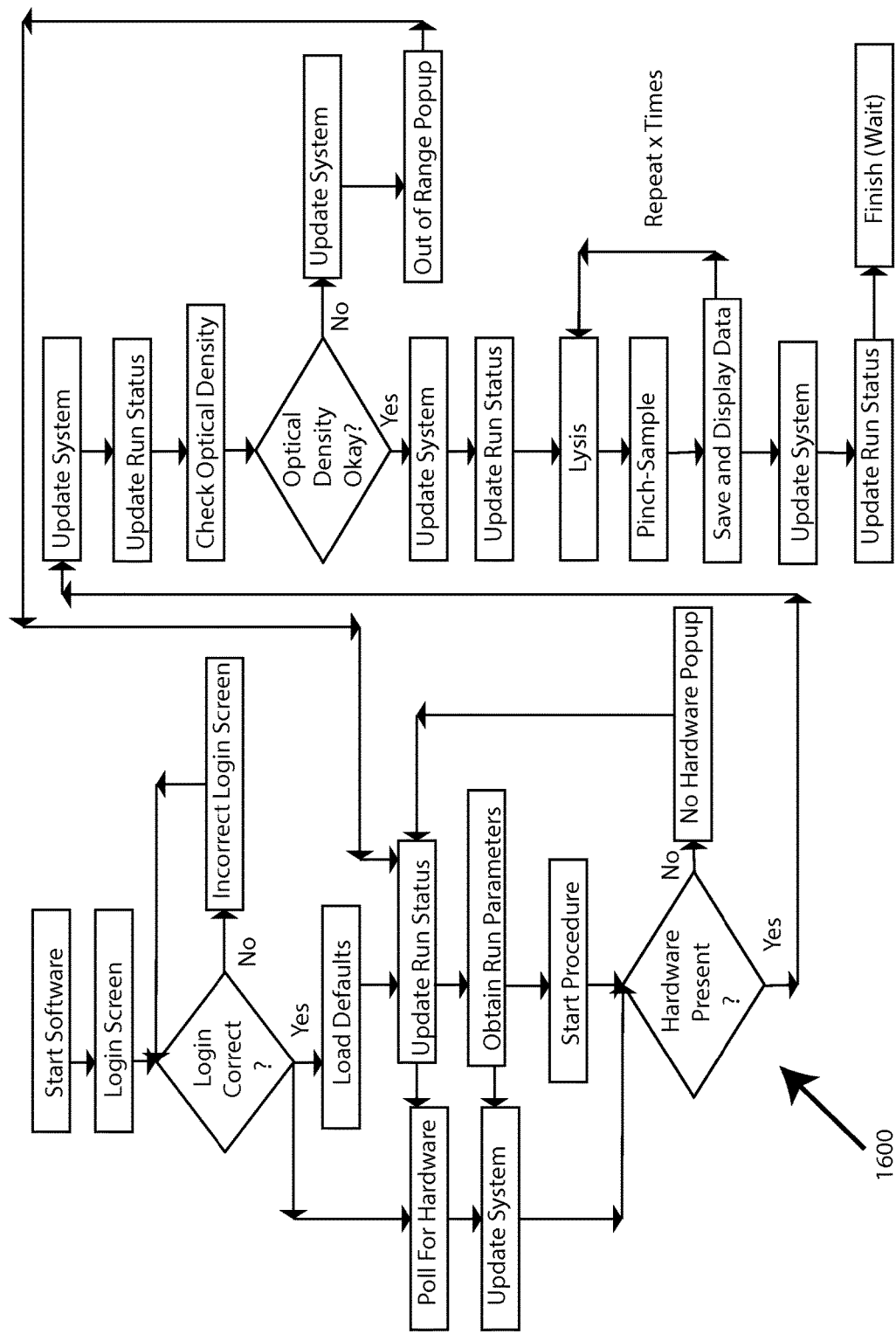
FIG. 16 shows an activity model.

FIG. 16 shows an activity model 1600.

Figure 17:
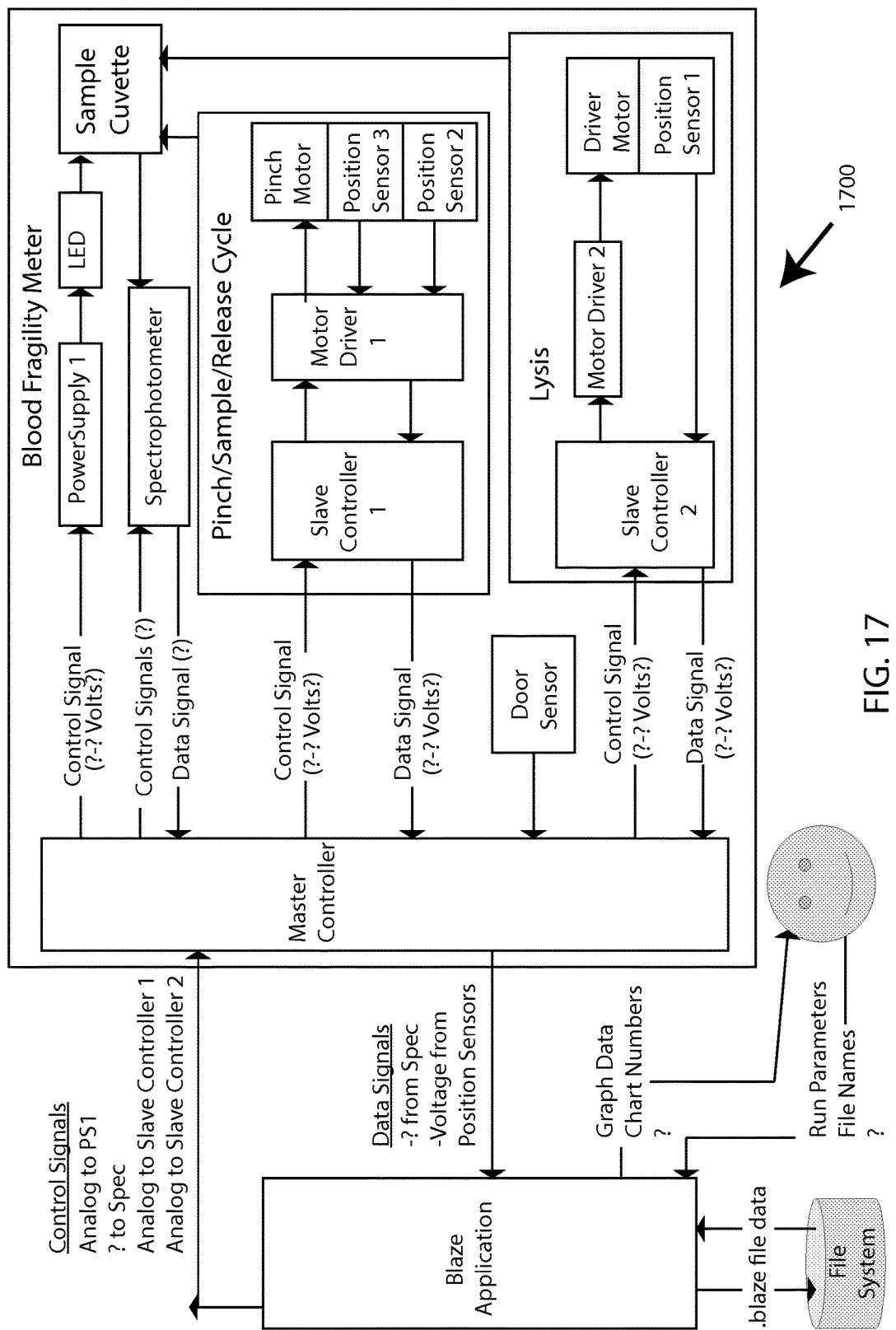
FIG. 17 shows a software context diagram.

FIG. 17 is a software context diagram to help illustrate how the described software architecture model fits in the context of the overall system 1700.

This disclosure next describes system integration for overall operation of MF testing. While certain example components may be indicated depending on the level of detail exhibited in any given example diagram, these depictions can largely apply interchangeably to various combinations of components or subsystems that are consistent with any embodiment in the overall inventive scope (e.g., electromagnetic motion vs. mechanical motion of bead, spectral vs. cell-counting detection of lysis, etc.), and should be interpreted accordingly.

Figure 18:
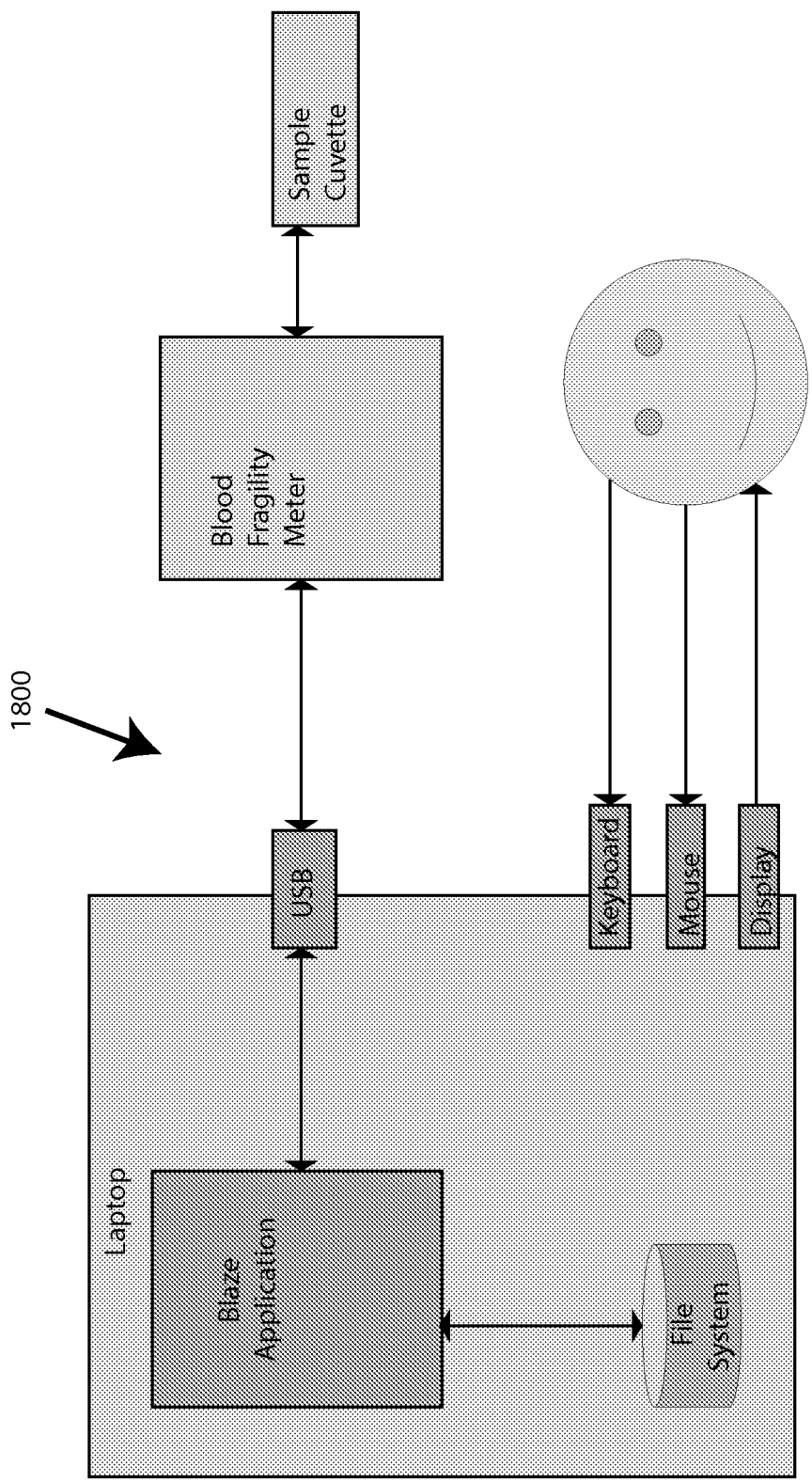
FIG. 18 shows a high-level system-architecture diagram.

FIG. 18 shows various described aspects of the present invention, in the context of a "high-level" system-architecture diagram 1800.

Figure 19:
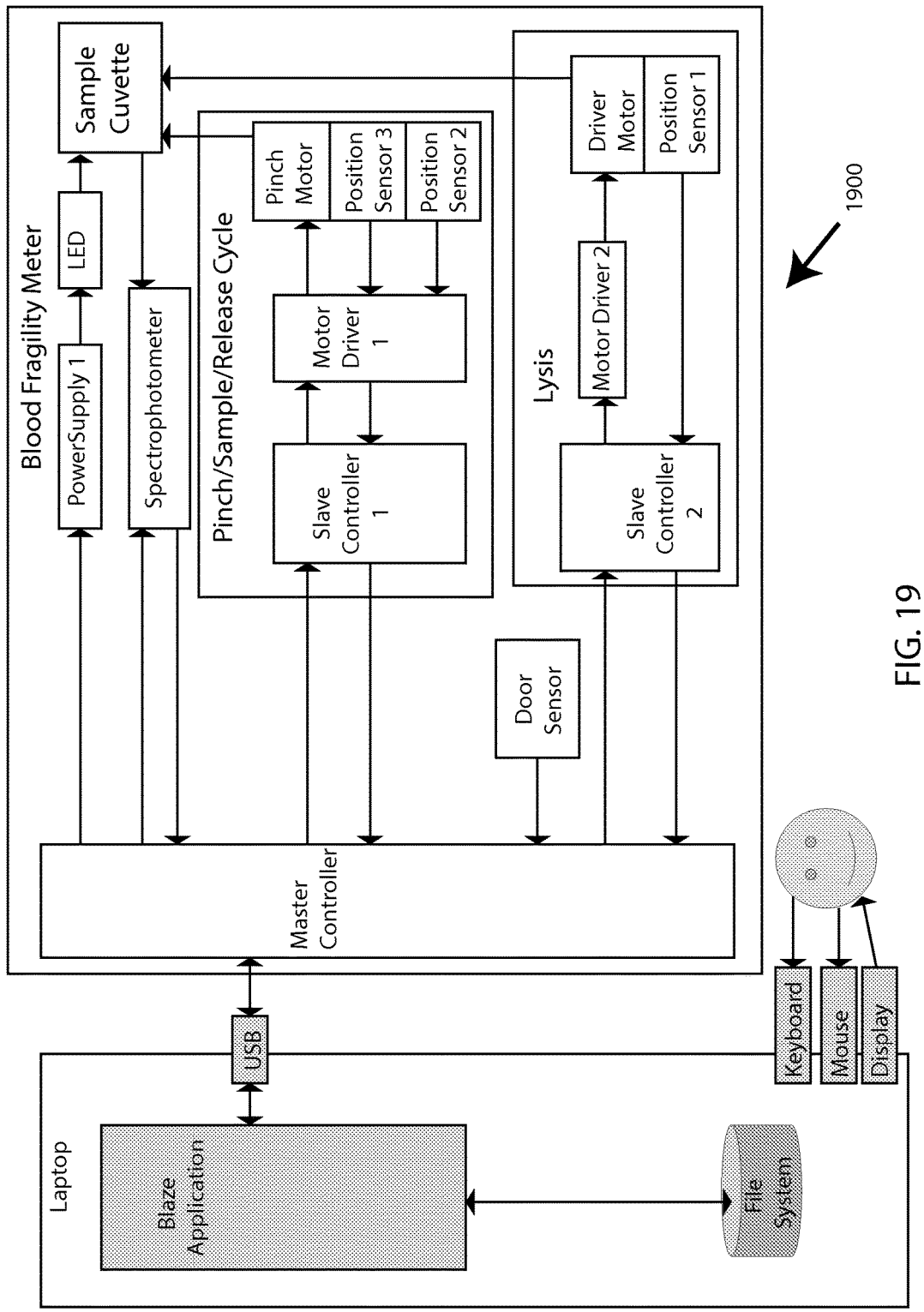
FIG. 19 shows a system-architecture diagram.

FIG. 19 then elaborates on the high-level diagram with a more detailed system-architecture diagram 1900.

This disclosure next details an example embodiment of a MF testing machine of a linear horizontal bead-milling type, in the context of included drawings.

The main system components for this example embodiment are: a sample cuvette/cartridge assembly (contains the sample and a bead to mechanically lyse cells), a carriage (holds sample cuvette during operation and rides on linear rails), miller (in this case, a motor that drives a crank and connecting rod to turn rotary motion into linear motion in the carriage that drives the ball through the sample, with a position sensor that tells system when a safe carriage position has been reached to perform analysis), pincher (in this case, a motor and connecting arms that address/bring the illumination and detections optics to the sample; this system creates proper sample thickness(es) for analysis, which might be defined by a predetermined gap length or predetermined characteristics for the optical results; this system also controls a magnet that draws the ball out of the pinch-zone during its operation), LED light sources (wide spectrum (VIS+UV) combined light source to illuminate the sample), spectrometer (detector that collects and analysis the wavelengths of light from the sources transmitted through the sample), analysis optics (components that connect the source illumination and detector to the sample cuvette), control electronics (to connect the system to the system GUI to control operations of the other sub-systems; includes power distribution from the supply and detection of sensor and switches (including door interlock)).

Figure 20:
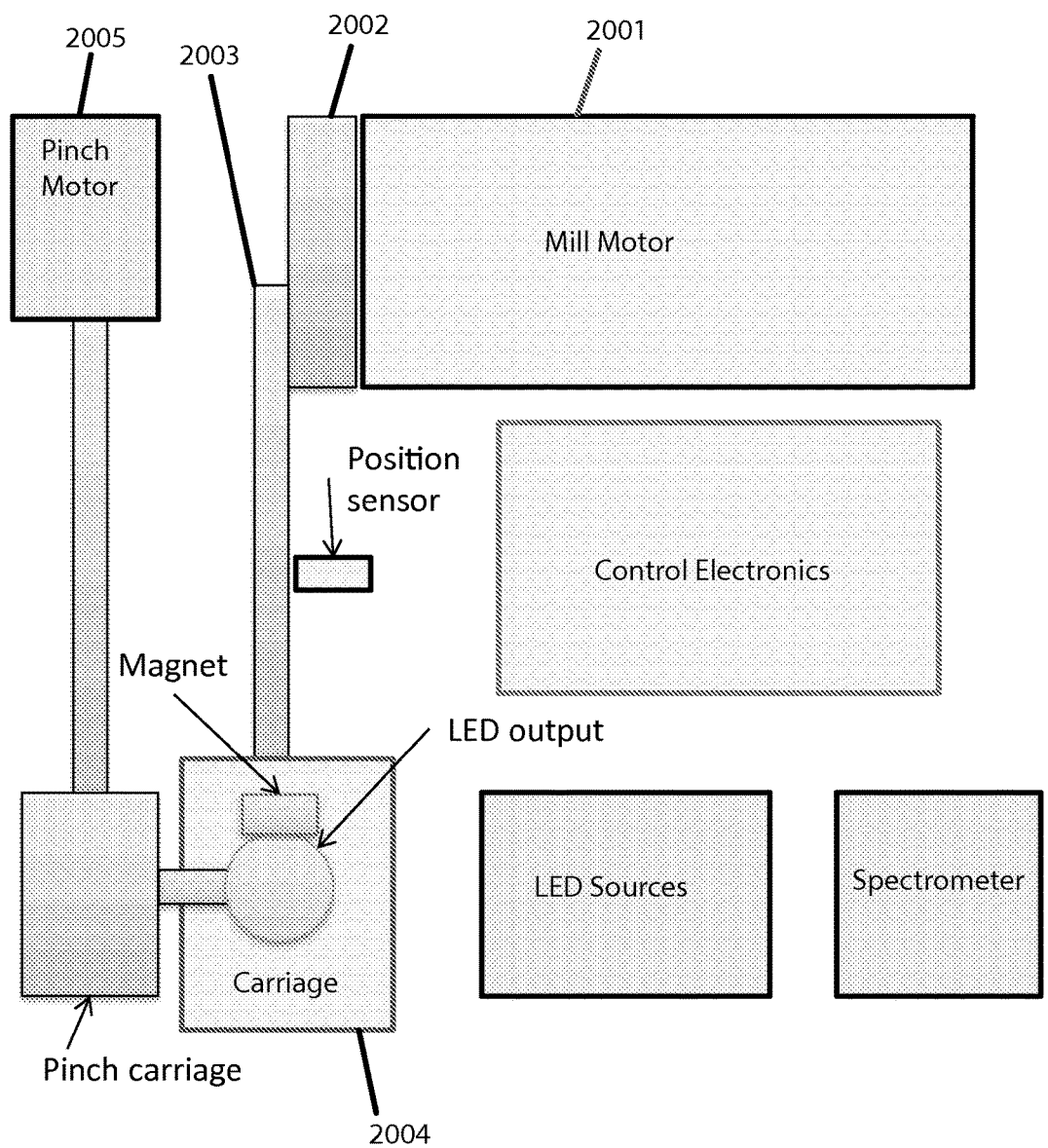
FIG. 20 shows a block diagram of system elements.

A block diagram depicting a "top view" of system components appears in FIG. 20. The shown elements of this example embodiment interact as follows: To agitate and stress a sample, a mill motor 2001 turns a crank 2002 and thus a connecting rod 2003 to translate rotary motion to linear motion for the carriage 2004. To take optical readings intermittently, the carriage is pinched by a pinch motor 2005 which turns a long threaded screw connected to two joined sliding members to translate the rotary motion to dual linear motion to concurrently bring in a light terminal from the top and a spectral detector from the bottom (not shown).

Figure 21:
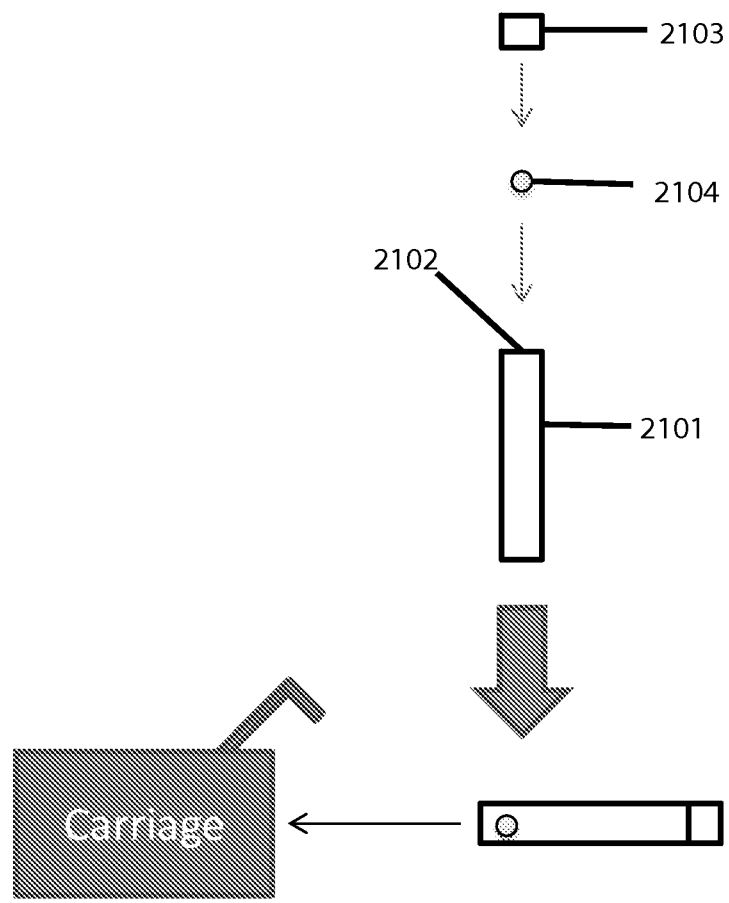
FIG. 21 shows a block diagram of a sample-holding cartridge.

A block diagram of a sample-holding cartridge (which also serves as a "cuvette" in this case) appears in FIG. 21. The shown elements of this example embodiment relate to each other as follows: The cuvette main body 2101 is where a testing sample gets placed via an opening 2102 that is closed with a cap 2103. Any suitable (e.g. sufficiently strong) capping means could be employed here (e.g. threaded screw type, snap type, etc.). A bead 2104 also goes in said main body, whether manufactured to be there initially or placed by a user. The closed/capped cartridge or "cuvette" then goes in the carriage.

Figure 22:
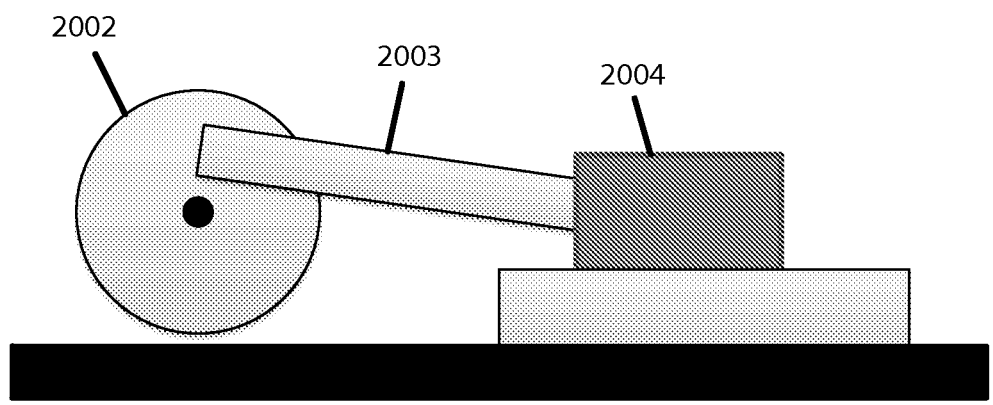
FIG. 22 shows a translation of rotary motion to linear motion.

The translation of rotary motion to linear motion is specifically depicted by FIG. 22, which shows the crank 2002 (turned by the mill motor) which moves the connecting rod 2003, to cause the carriage 2004 (which holds the cuvette, which contains the bead) to move back and forth.

Figure 23:
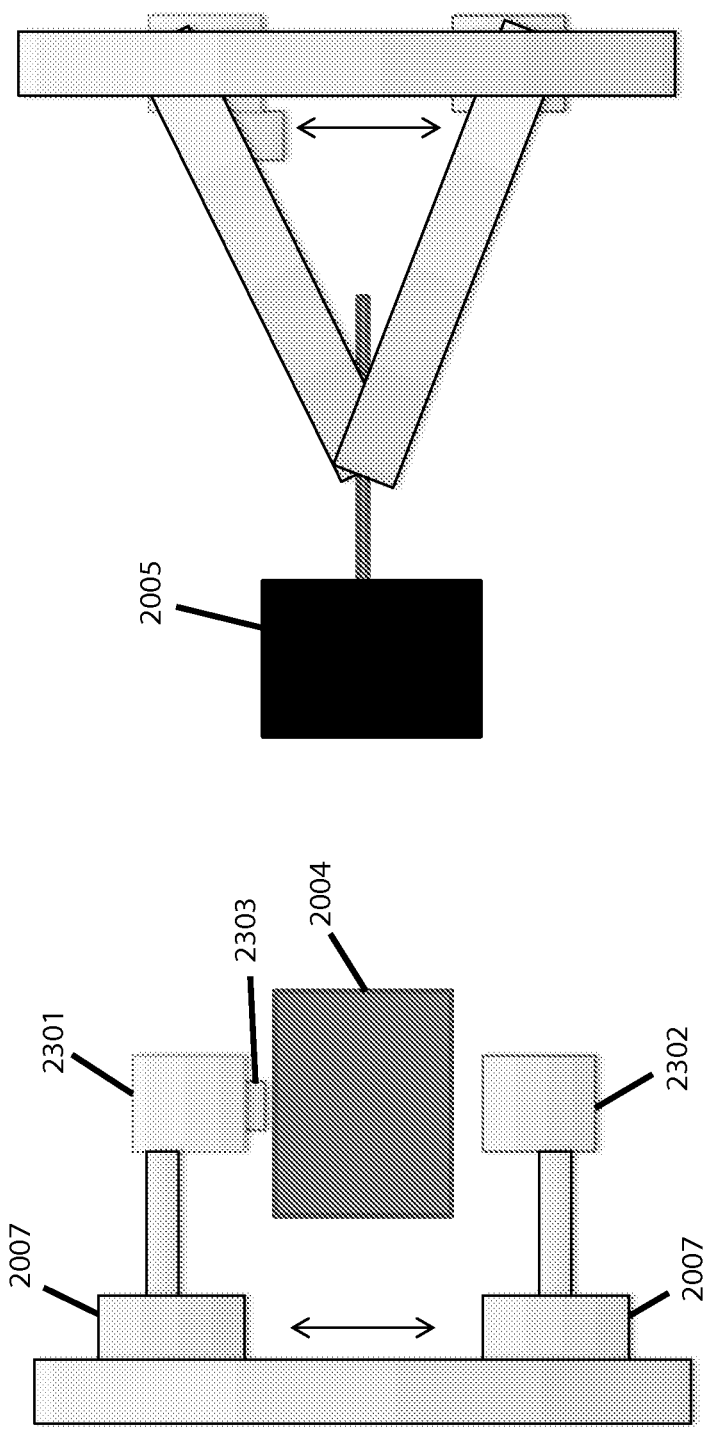
FIG. 23 shows pinch mechanics and optics.

Pinch mechanics and optics are specifically depicted in FIG. 23. The pinch motor 2005 causes two sliding members 2007 to push and pull the LED output source 2301 and spectrometer input detector 2302 to and from the cuvette in the carriage 2004, to reach an appropriate thickness for optical readings between intervals of bead agitation of the sample. A magnet 2303 on one side pulls the (magnetic, in this case) bead out of the way for the pinching. The sliding-members approach, via screw threads turned by a stepper-motor, translates rotary motion to linear (and in this case, vertical) motion; this, or a similarly translational mechanism, is preferred over using two separate motors.

The pinching motor strength should be commensurate with any resistance offered by the flexible material or portion(s) thereof to be compressed (for adequate speed/control of compression), which may in turn depend in part upon the thickness of the material(s) being used for the compressible portion (see below for relevant discussion on the cartridge). Any stepper motors employed would likely be controlled via firmware, as an intermediary between the software and the actuators, as is common with such electromechanical technologies.

Figure 24:
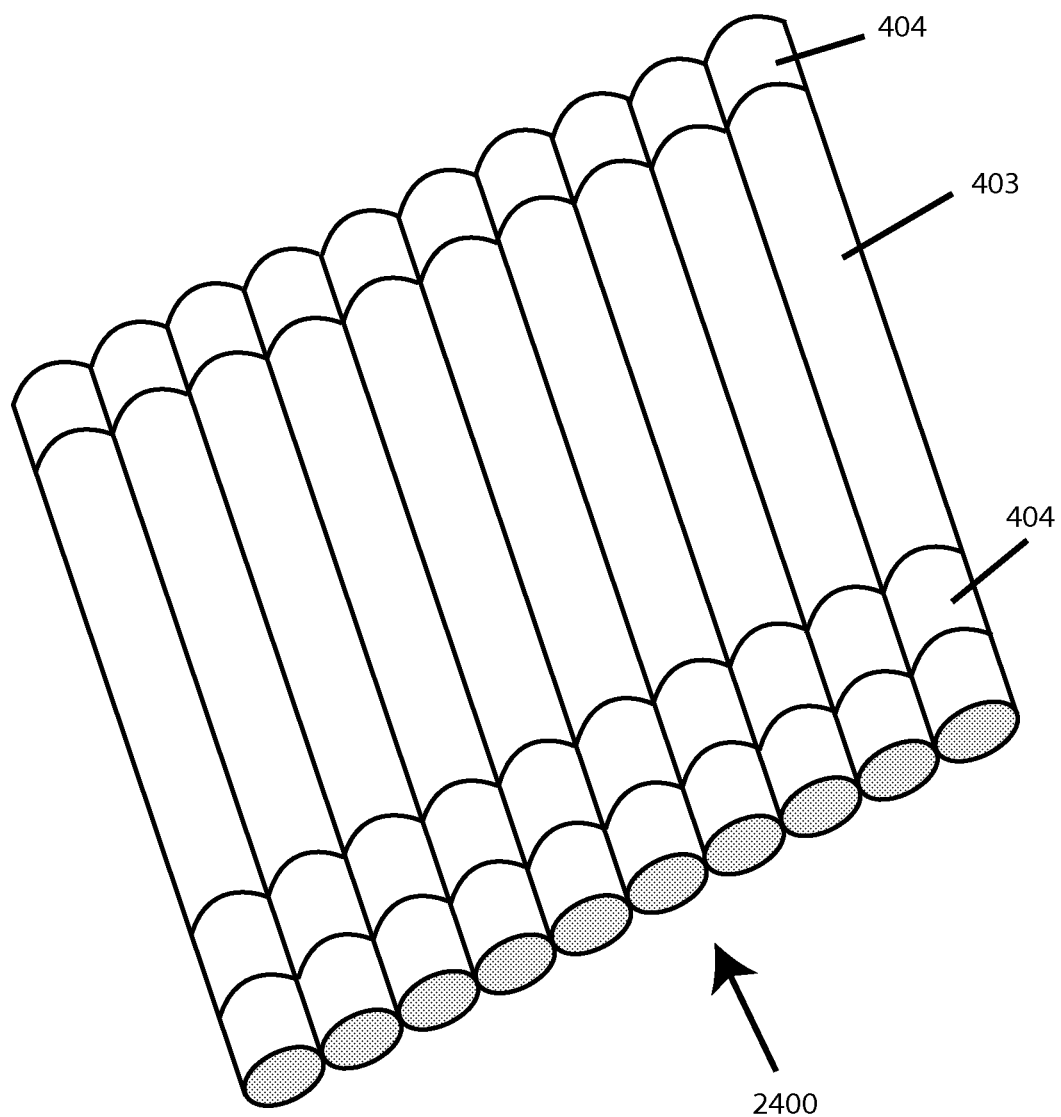
FIG. 24 shows a multi-plexed cartridge.

This disclosure next details possible materials and configurations for embodiments of a sample-holding cartridge device (preferably disposable, and preferably designed for single-use) for embodiments of an RBC MF tester. Refer back to FIG. 4 for a generalized illustration of an embodiment of a sample-holding cartridge (in the context of an overall testing system), and the description thereof for an overview of the main aspects of such embodiment. Also, see FIG. 24 for a depiction of such a cartridge "multiplexed" 2400 or multiplied in parallel to enable testing of multiple distinct samples or subsamples concurrently.

There are several industry standard (i.e., pre-manufactured) plastic materials already in use in blood related applications such as intravenous tubes or surgical operations. Custom compounded and/or coated or treated formulations may also be employed if desired. Tygon® material in general, currently formulated and produced as a proprietary family of robust plastic or polymer tubing varying in base materials constituencies, can in many cases offer good reversibility of compression (i.e., de-compressibility) upon release, and (somewhat relatedly) is manufactured in relatively high thicknesses—this can present a challenge for optical detection in some cases; a solution to this that still retains the overall thickness and post-compression "spring-back" is to have small shaved or otherwise thinned "window" portion(s) of the tube for optics, while the majority of the tube constitutes much or all of the rest of the longitudinal body of a cylindrical cartridge (which still may have end caps and/or a structural component such as an overmold or exoskeleton, in addition to the flexible tube material). Alternatively, an appropriate balance or tradeoff among tubing thickness, flexibility, resilience, and transparency may be selected from existing products to allow using tubing as-is "off the shelf." Resistance to flex-fatigue is an important consideration for repeatably-reversible pinching or other compression over sustained usage.

An alternative to flexible tubing could employ sheets of LDPE, or low-density polyethylene, as an example material for a membrane portion(s) of a disposable cartridge. Sheets or "films" (which are manufactured with notable differences from "tubing" such as the above-noted Tygon) could be heat-staked about a rigid skeleton—which in the above example cylindrical cartridge includes "wings" alongside the cylinder (i.e., aiding with handling/insertion guidance and subsequent stability, as well as definitional structure) and circular "rings" at either end of the cylinder. Of course, cylindrical/round shaping is not needed—but may facilitate the use of spherical beads as well as other non-custom parts. If using plastic "tubing," rather than sheets/films, the extent of structure needed to be provided from an overmold/skeleton or the like can become somewhat simpler such as a cage or mesh or the like (in part depending on the properties and tolerances of the tubing), and in some cases could be omitted altogether (though some sort of structural assistance is preferred, or at least a tacking point(s) to hold securely in position during testing). Alternatively, it could use an essentially full encasement, such as with a rigid tube exterior to the flexible tube.

Figure 25A:
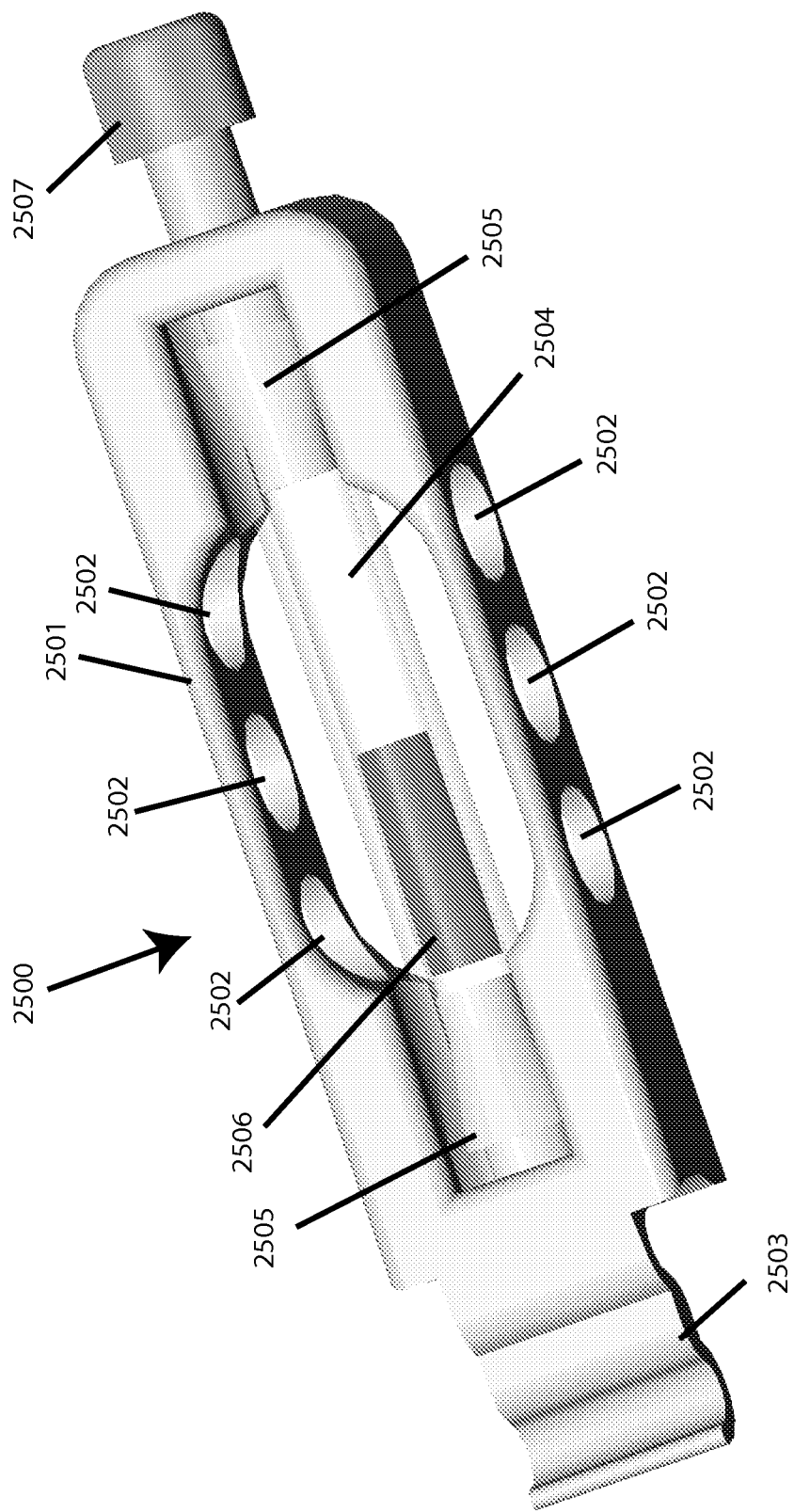
FIG. 25A shows a perspective view of a plastic-tubing based embodiment of a single-sample-holding cartridge.
Figure 25B:
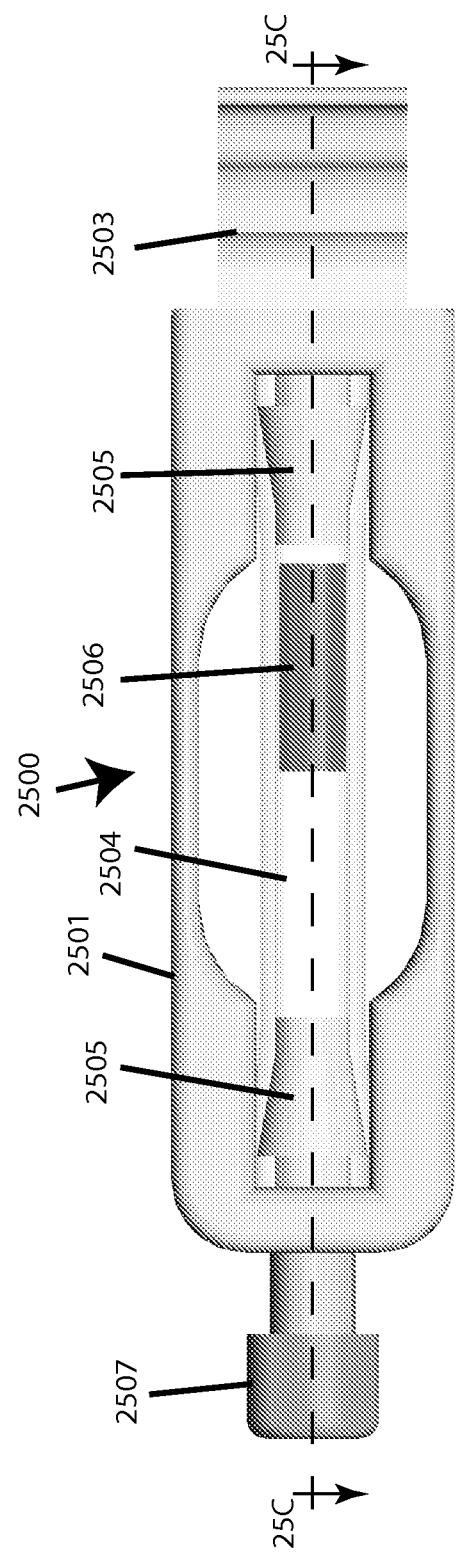
FIG. 25B shows a top view of a plastic-tubing based embodiment of a single-sample-holding cartridge.
Figure 25C:
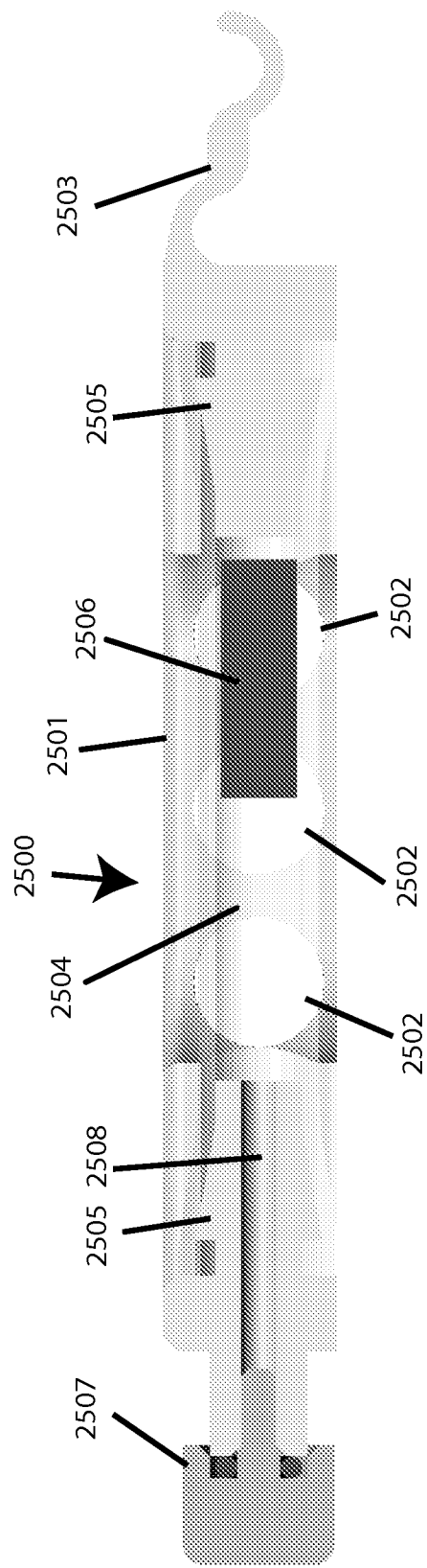
FIG. 25C shows a cross-section view of a plastic-tubing based embodiment of a single-sample-holding cartridge.

In the example cartridge embodiment depicted in FIGS. 25A, 25B, and 25C, the overall cartridge 2500 includes a cartridge body 2501 featuring ventilation holes 2502 and a capturing hook 2503 for attaching to the machine (described below). Said body holds/contains a piece of pre-manufactured flexible clear tubing of appropriate thickness to be sufficiently compressible and resilient, which provides a sample cavity 2504. Barbed plugs 2505 are on each end of the tube, confining a coated magnetic bead 2506, with the "top" one of said plugs being hollowed to provide a capillary 2508 for inserting the sample (e.g. via pipette tip, such as used for loading electrophoresis gels) before the sealing plug 2507 is secured (e.g. via screw-threads). Upon pinching at the cavity area between successive intervals of milling, sample inside is temporarily pushed away from the light path as part of the tubing shape gets reversibly compressed to allow taking an optical reading through said tubing. There may be a separate window to facilitate calibration or baselining (not shown), which alternatively could be located on the machine itself (note this may be for example a piece of the clear plastic tubing being used in the cartridge, for the "clear/light" calibration, as well as having an opaque portion to be used for "blackout/dark" calibration). A fill-line may be set to allow for a small/acceptable amount of air to remain after sealing by the user, to minimize risk of sample spillage or overflow. [Note that it may be acceptable in some cases to specify that users should only use samples with minimal auto-hemolysis, to simplify determination of a "0% lysis" measurement. For determining "100% lysis," as a fractional denominator, options include either running the test until a fragility profile plateaus (and thus renders the total hemoglobin approximately inferable), or employing spectral measurement in the visible range (via known means).]

Whatever form the body of such a cartridge takes, portion(s) must be strong enough to withstand any force from repeated bead impact (e.g. via end-caps, plugs, or the like), while at least part of the wall(s) be relatively manipulable for pinchability (e.g. plastic-based film or tubing, likely polymer-based). It is possible for the entire cartridge body to be non-rigid, provided sufficient strength (e.g. end-welds/seals) and structural definition exist. In general, a reversibly flexible and pinchable portion is the preferred way to achieve a compressible portion of a stressing chamber to achieve an optically-appropriate gap, to in turn facilitate lysis measurement after or between defined stressing session(s), and various possible plastic formulations could serve sufficiently for such. And in general, the optimal materials and configuration may depend in each case on a variety of application-specific factors, and can be fairly adapted accordingly as desired. It may also facilitate optimal function to take measures to minimize sample foaming during agitation, whether through anti-foam interior cartridge material properties or treatments and/or appropriate dimensional or volume or fill-fraction considerations (e.g. through minimizing or trapping residual air within the cartridge interior), etc.; the latter may require a balance of concerns, as filling to near-capacity for example may be more functionally feasible with a relatively more flexible tube. Sample insertion or filling (and subsequent closing/sealing) by the user can be done by various means, depending on how much convenience is being prioritized over cartridge complexity. It has been observed that consistent fill fraction is important to the results, so designs (e.g. via end tip configuration) which ensure essentially 100% filling may be preferred because this provides both consistency and foam minimization (the latter being due to the lack of air in the cartridge), though a small amount can still be acceptable.

Figure 26:
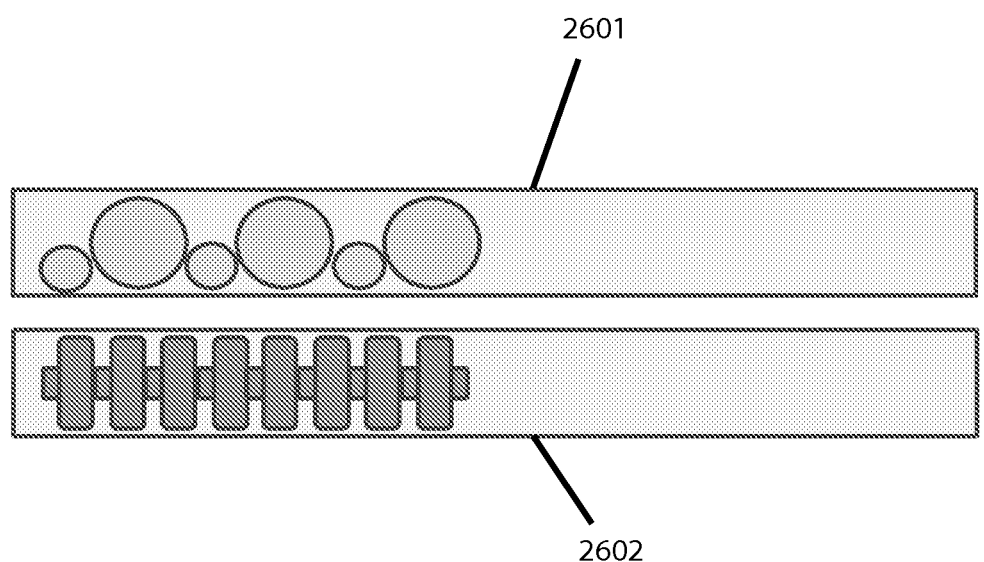
FIG. 26 shows examples of non-conventional bead designs.

Regarding the bead or slug or plug or like object(s) within the cartridge to facilitate sample lysis, preliminary experimentation has found that a typical single smooth spherical bead may not provide the desired lysis efficiency. For example, a conjoinment or other combination of multiple beads of varying or alternating shapes or diameters (such as alternating small-large), or some resemblance of this approach via a single object, may improve lysis efficiency. The pitch, width, number, and depth of the grooves/ridges or surface texturing, as well as the relative length of the bead and cartridge interior, can all contribute to lysis efficiency; this can be experimentally calibrated for any given configuration to determine the desired level of efficiency. Preliminary experimentation with non-conventional beads indicates that factors such as cartridge interior shape/geometry, size/dimensionality, volume, and fill-fraction (for example) can be relevant and should be considered. For cylindrical tubing as the chamber, an essentially cylindrical bead was found to be superior to spherical beads in lysis efficiency, and ridges further improved upon this, as did a knurled surface. Moreover, the ratio between the bead/slug length and the interior length of the lysis chamber was a significant factor, with a ratio between 0.5 and 0.8 being most efficient for lysis in cases where the chamber is fully filled. Anything that can improve lysis efficiency can be desirable for making the test faster and/or reducing the energy use and associated heat generation, etc. Instead of or in conjunction with grooves or ridges, having multiple objects nested (e.g. concentrically) can also provide additional stress, though this approach would work better when using non-magnetic beads/objects. Also possible is to texturize the interior surface or the cartridge wall. If a small gap between the bead and the cartridge wall interior is desired to aid stressing efficiency, then for a non-cylindrical cartridge the bead would not be round or cylindrical but would have a similar cross-sectional shape to that of the cartridge. FIG. 26 shows some possible alternative bead configurations, with the one 2601 being conjoined spheres of differing diameters and another 2602 having a longitudinal rod with spaced discs.

This disclosure next describes select approaches to electromagnetic actuation for a bead mill (whether for general use or for an MF tester). One example found by inventors to be well-adaptable to controllable bead-milling, whether as part of fragility testing or for other bead milling, is to make an electromagnetic actuator of the sort from an audio speaker, which was found to be appropriately controllable to give an adequate range of linear excursion at a useful range of oscillation frequencies (going as low as 1 Hz, and as high as at least 30 Hz, and adjustable in increments as fine as 1 Hz). Note that higher frequencies were found to reduce the range of motion, so the particular parameters would ideally (but not necessarily, particularly for plain bead-milling rather than MF testing) be selected and/or modified to ensure adequate distance travel over the full desired range of frequencies. A difference from an "electromagnetic bead mill" as described earlier herein is that there the electromagnet targeted the bead itself—rather than the cartridge as in this case.

Inventors found through experimentation that there are commercially-available electromagnetic (EM) actuators (e.g. ButtKicker™, a line of low-frequency audio transducers utilized to agitate special seats in movie theatres, instead of certain voice coil shakers or other tactile devices) that can be readily adapted to propel either an entire cartridge containing a bead or just a magnetic bead therein, albeit more readily so for the latter. (A tradeoff to consider when selecting between these two approaches is that to move only the bead, the bead is limited in composition to sufficiently magnetic material. This may require an exterior biocompatible coating, especially as oxidation can be a greater risk with magnetic or otherwise magnetically-susceptible objects versus stainless steel (for example). Moving only the bead also notably minimizes vibration, which is often a priority.) For multiplexing, a more custom coil-based EM configuration might be preferable to provide more flexibility on the spatial orientation (at least for use in a MF tester, to facilitate accessibility for optical detection—which would of course not be needed for simple bead-milling in general). More details about the technologies employed in some seat-agitation types of products can be found for example in International Patent Application Publication Numbers WO2003069299 (entitled "Electromagnetic Shaker") and WO2000005805 (entitled "Low Frequency Vibrator).

Figure 27A:
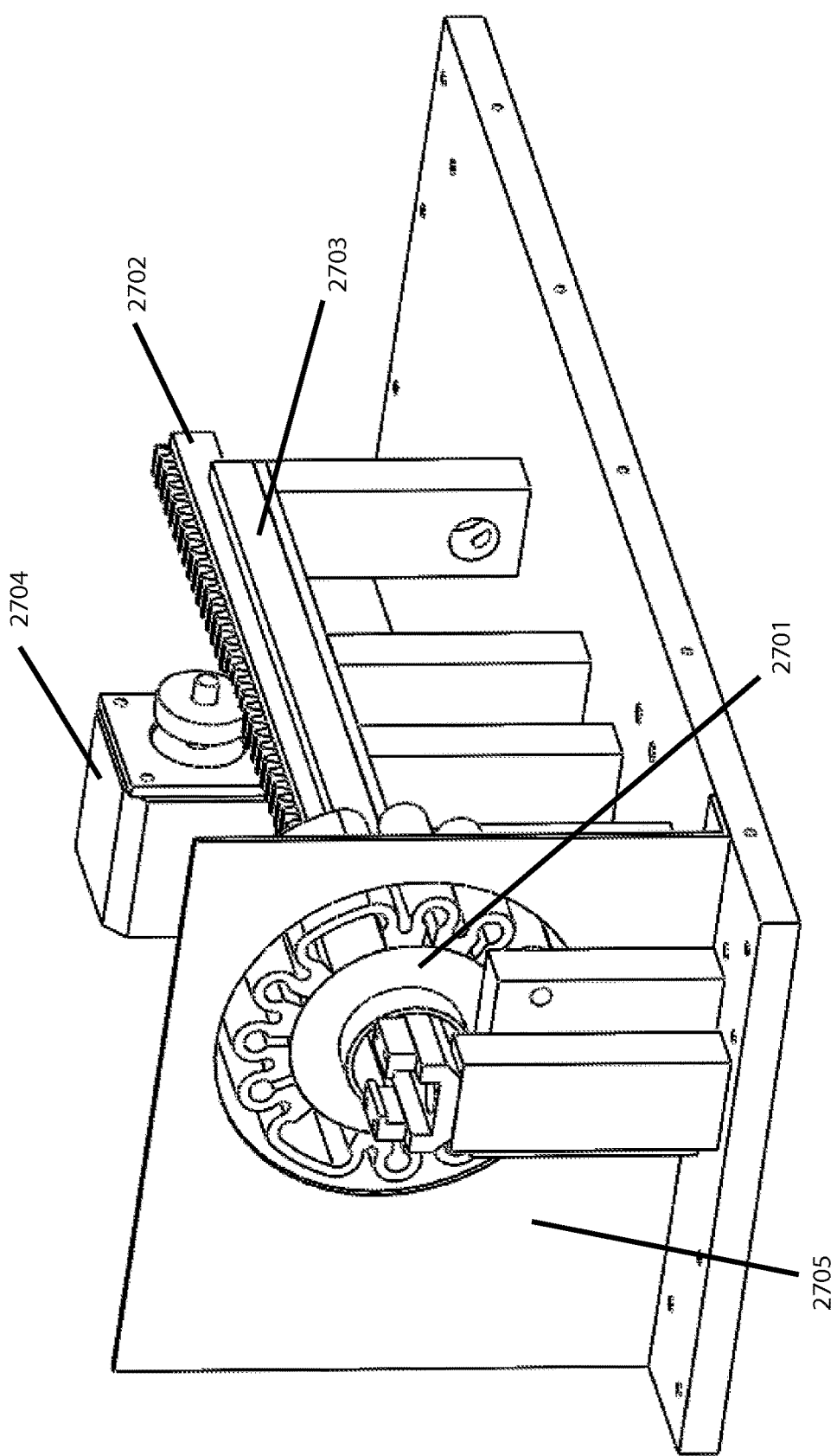
FIGS. 27A and 27B show an electro-magnetic (EM) embodiment of a bead-mill.
Figure 27B:
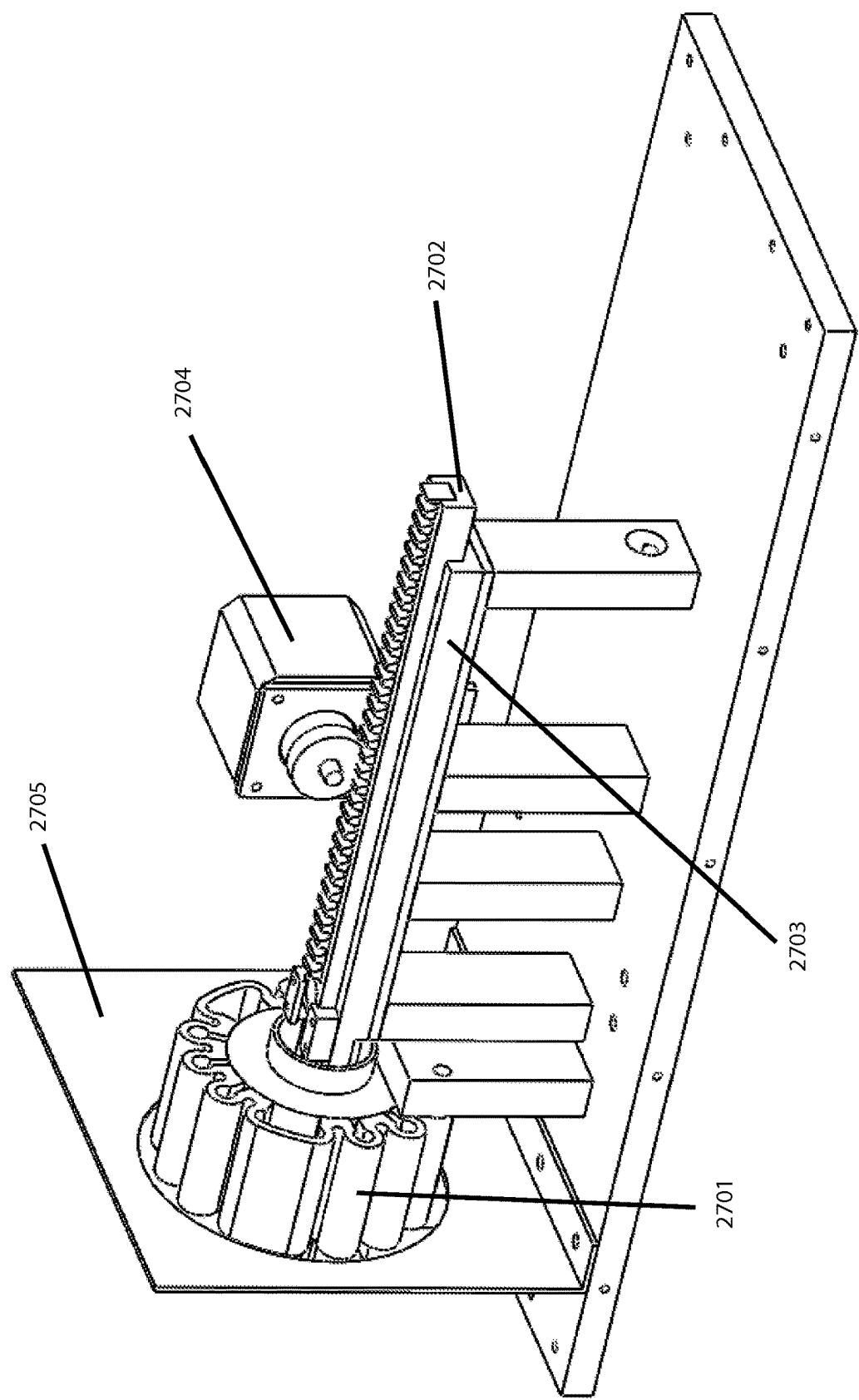

In the example bead miller embodiment depicted in FIG. 27A and FIG. 27B, which employs the magnetic-bead approach that avoids having to shake the entire cartridge, a low-frequency audio transducer serving as an electromagnetic bead actuator 2701 here essentially is adapted from one of the commercially-available seat-agitation products noted above. FIG. 27A is a perspective front view and FIG. 27B is a perspective back view. (By default it comes with a magnetically suspended piston that moves precisely in response to amplified audio signal input; the mass can generate a high force that can be accurately transferred to whatever the housing is attached to (which is more relevant for the "cartridge-shaking" embodiments, rather than the direct "bead-moving" embodiments.) For embodiments like this one, wherein the cartridge is stationary and the bead is moved by direct magnetism, the cartridge is positioned such that the magnetic bead inside of the cartridge is directly movable by the transducer. In practical use, most plain bead mills will be multi-plexed to allow several samples to be milled simultaneously; this can be done by using multiple of such audio transducers or other coil-based EM actuators, and/or the direct "bead-moving" approach by placing multiple tubes in the EM "sweet spot" (the particular location and size of which depends upon the particular configuration employed) where the field causes magnet oscillation. And of course, for just a plain bead mill without fragility testing, no flexible or "pinchable" portion for pinching/compressing is needed in the tube(s). Because the bead miller version shown in FIG. 27 is specifically designed to be incorporated in the fragility-testing machine (described subsequently), which is an embodiment designed to incorporate a commercially-available EM actuator, it also depicts a cartridge carrier 2702 that slides along a cartridge rail 2703 as driven by a cartridge loading motor 2704, to provide movement of the cartridge(s) to and from the region of bead actuation/movement (such as to and from the region of optical detection, after respective stressing intervals). A thermal baffle 2705 may be employed to direct air flow from fan(s) (not shown), as desired (note that temperature is more often a concern with fragility-testing versus with plain bead-milling).

Figure 28A:
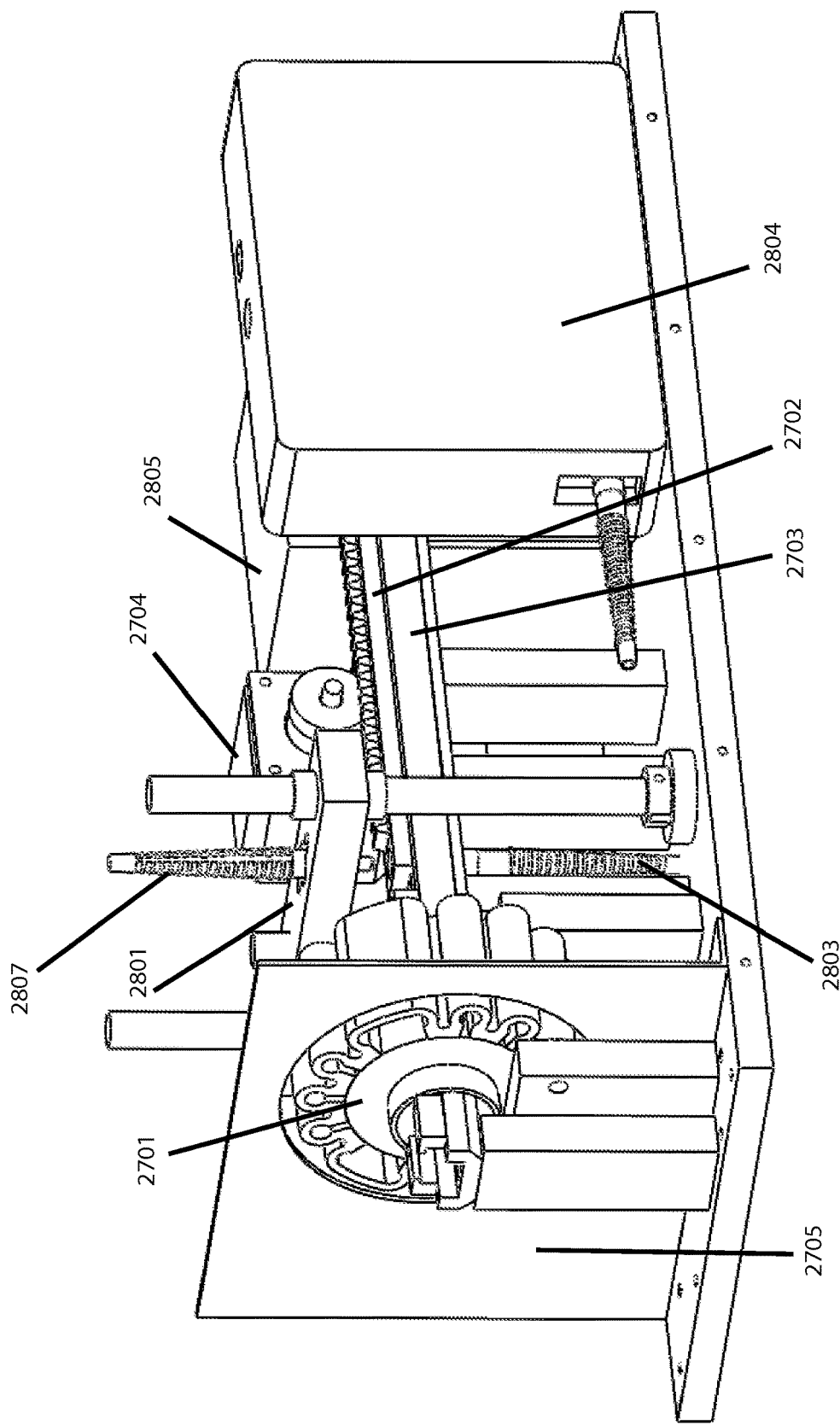
FIGS. 28A and 28B show a mechanical fragility tester utilizing an EM bead-mill.
Figure 28B:
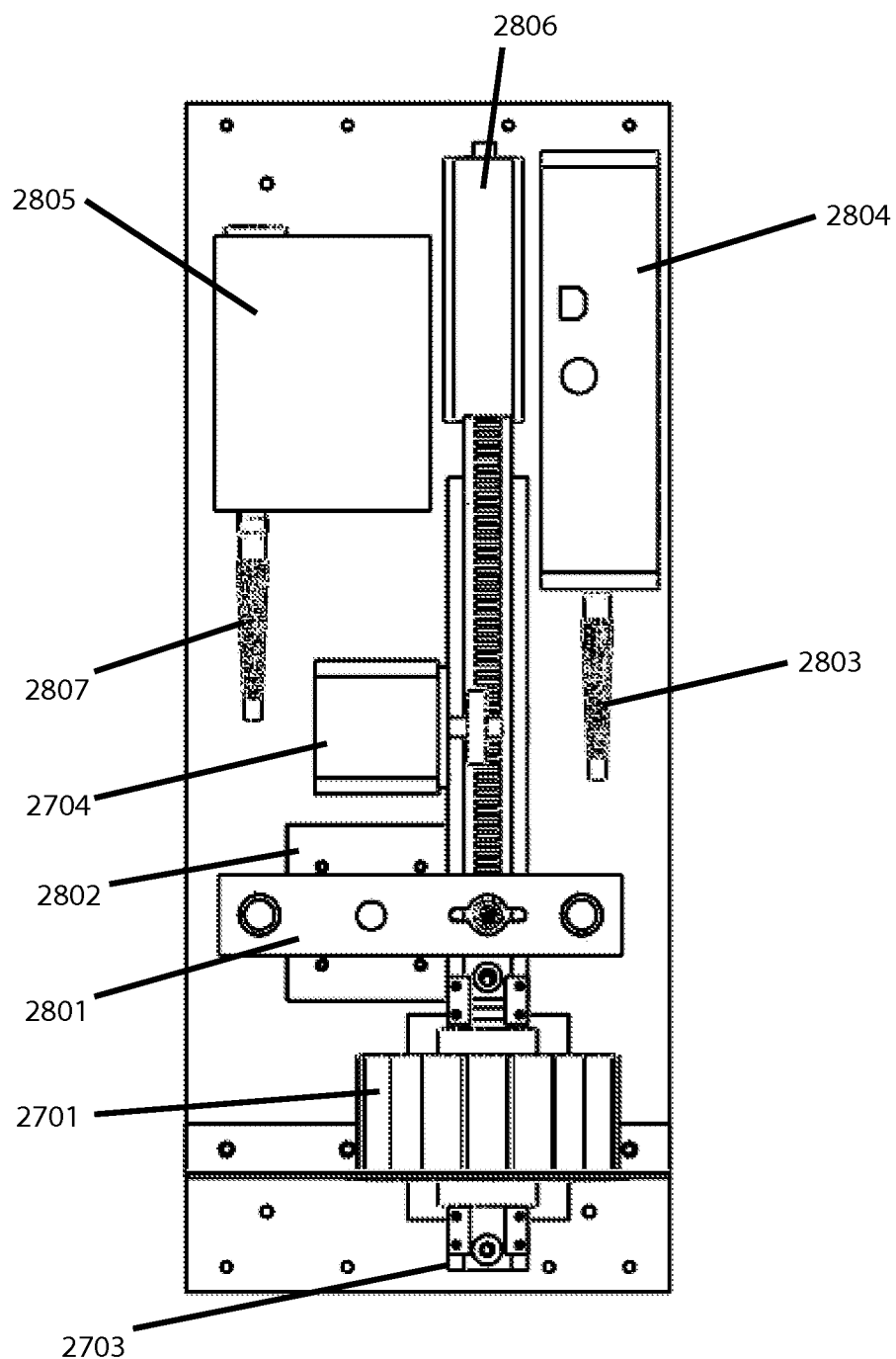

FIGS. 28A and 28B then show an example of an overall MF tester utilizing the bead miller shown earlier in FIG. 27. FIG. 28A is a perspective view and FIG. 28B is a top view. In addition to elements discussed above, there is a pole-and-bar based pinching mechanism 2801 driven by a pinch drive motor 2802 to repeatedly compress the cartridge between milling intervals while the sampling fiber optic 2803 gathers readings for the spectrophotometer 2804 indicating what fraction of hemoglobin is extracellular versus intracellular (as indicative of percentage hemolysis) per the above-noted optical technology. A fiber-coupled light source 2805 and associated LED controller 2806 serve to provide the light during these readings, through an illuminating fiber optic 2807. Said fiber optics can be brought toward the cartridge/sample during the pinching. Also, if taking multiple optical readings (e.g., for confirmation or averaging) upon each respective stressing increment, the controlling program can if desired have the cartridge slide once past the magnet, via the rail, in order to let the bead essentially "mix" the sample between said repeat readings.

This disclosure next addresses a few miscellaneous general points regarding the overall test system and approach.

In general, fixed or normalized dilution of cell concentrations can be performed either by the user or be automated in the system. Alternatively, the consumable/disposable piece could be pre-filled with appropriate buffer from manufacture. Depending on the limitations of any given version/embodiment configuration, usage instructions may specify a range for hematocrit or red cell concentration that users should stay within—to maintain a given level of accuracy.

It's important to contrast any kind of RBC "fragility" with the related property of cell "deformability"—which is a broad concept covering many different kinds of tests that all in some way seek to determine how well a cell can deform or change shape under stress. Moreover, fragility (MF in particular) is particularly well suited for multi-parameter (>1) stressing to give multi-dimensional (>2) profiles showing how hemolysis depends on two or more stress variables such as extent/degree of intensity and extent/degree of duration (for one or more given type/kind) of mechanical stress. Indeed, merely providing the available option of such data richness can potentially enhance the general utility of embracing MF over other membrane-related metrics.

The fragility testing system described herein could also potentially be adapted to test mechanical fragility of material other than red blood cells. Of course the stressor(s)' selection and overall system configuration would need to be empirically assessed and modified as appropriate to suit such alternative material, and for a type of cells or tissue (for example) other than red blood cells an appropriately modified spectral or cell-counting approach (if applicable) to detection of lysis/rupture would be needed.

For purposes herein, "bead" and like terms includes broadly any item or object whose presence in a sample serves to directly or indirectly cause or facilitate rupture or disruption, such as cell lysis. "Mill" and its variants refers broadly to any use of bead movement to create mechanical stress. "Cartridge" refers to any container that holds a sample while it gets milled, and in the context of RBC fragility testers, also contains the sample while hemolysis gets detected, preferably via pinching (and preferably in the same portion of the cartridge, to avoid a need to transfer the sample between the stressing and the detection). "Pinching" causes at least a portion of a sample to thin in shape, to facilitate detection.

This disclosure is enabling to those of ordinary skill in the art, while maintaining adequate flexibility for reasonable adaptation. Moreover, those skilled in the art will appreciate variations of the examples and principles described herein, which are also intended to be within the scope of the present invention. Any references herein to "the invention" or the like are thus intended in this spirit, always in consideration of the respective context.

We claim:

1. A machine configured for testing mechanical fragility of cells, the machine comprising:
   a sample miller for moving a bead residing within a sample comprising erythrocytes within a stressing chamber, wherein the stressing chamber is configured to cause hemolysis in said sample;

a chamber pincher for reversibly compressing an optically transparent portion of said stressing chamber to a thickness suitable for an optical measurement to quantify said hemolysis;

means for positioning the bead away from the optically transparent portion of the chamber before the optically transparent portion of the chamber is compressed by the pincher;

an optical detector for said optical measurement to quantify said hemolysis; and a light source for said optical detector.

2. The machine of claim 1, wherein said sample miller comprises a motor from which rotary motion is translatable into linear motion, such that said bead is movable by moving said stressing chamber.

3. The machine of claim 1, wherein said sample miller employs a magnetic field.

4. The machine of claim 3, wherein an electromagnet is provided by an audio transducer.

5. The machine of claim 1, wherein said chamber pincher comprises a stepper motor drivable by firmware to bring a fiber optic to contact said optically transparent portion.

6. The machine of claim 1, wherein said light source comprises one or more light-emitting diodes (LEDs).

7. The machine of claim 1, wherein said thickness is a predetermined distance.

8. The machine of claim 1, wherein multiple optical measurements can occur during the compressing, and said optical measurement to quantify said hemolysis is selected from among said multiple optical measurements, based upon signal attenuation or calculated sample optical density.

9. The machine of claim 1, wherein separation of liquid and solid elements of said sample is not needed for said optical measurement to quantify said hemolysis and wherein the light source is configured to project light into and through the sample such that a portion of the light, having a wavelength of about 390-460 nm, is absorbed by a hemoglobin derivative in the sample and wherein the optical detector is configured to determine light absorption of the sample, within a wavelength of about 390-460 nm, to allow a determination of extent of hemolysis in the sample based on a relative proportion of a spectral peak that is unflattened.

10. The machine of claim 9, wherein said portion of the light comprises light having a wavelength of 418 nm.

11. The machine of claim 9, wherein another portion of the light comprises a wavelength of 576 nm.

12. The machine of claim 1, wherein said stressing chamber is provided by a single-use disposable cartridge.

13. The machine of claim 1, further comprising an electronic controller connecting said sample miller and said chamber pincher to a user-interface, said user-interface being either incorporated within or separate from the machine.

14. A machine configured for testing mechanical fragility of cells, the machine comprising:

a sample miller for moving a bead residing within a sample comprising erythrocytes within a stressing chamber, wherein the stressing chamber is configured to cause hemolysis in said sample;

a chamber pincher for reversibly compressing an optically transparent portion of said stressing chamber to a thickness suitable for an optical measurement to quantify said hemolysis;

a permanent magnet configured for positioning the bead away from the optically transparent portion of the chamber before the optically transparent portion of the chamber is compressed by the pincher;

an optical detector for said optical measurement to quantify said hemoloysis; and a light source for said optical detector.

* * * * *